United States Patent
Yu et al.

(10) Patent No.: US 7,884,142 B2
(45) Date of Patent: Feb. 8, 2011

(54) BIODEGRADABLE COPOLYMER AND THERMOSENSITIVE MATERIAL

(75) Inventors: Ya-Jen Yu, Taipei (TW); Chin-Fu Chen, Taipei (TW); Tsai-Yu Lin, Changhua (TW); Shao-Jen Yeh, Jhongpu Township (TW); Shian-Yih Wang, Taipei (TW); Po-Liang Lai, Changhua (TW)

(73) Assignee: Industrial Technology Research Institute (TW)

( * ) Notice: Subject to any disclaimer, the term of this patent is extended or adjusted under 35 U.S.C. 154(b) by 0 days.

(21) Appl. No.: 12/395,495

(22) Filed: Feb. 27, 2009

(65) Prior Publication Data

US 2009/0247666 A1    Oct. 1, 2009

(51) Int. Cl.
  A61K 6/00   (2006.01)
  C08G 69/14  (2006.01)
  C08G 75/00  (2006.01)

(52) U.S. Cl. .................. 523/118; 528/326; 528/337

(58) Field of Classification Search ............... 523/118
See application file for complete search history.

(56) References Cited

U.S. PATENT DOCUMENTS

| | | | |
|---|---|---|---|
| 4,188,373 A | 2/1980 | Krezanoski | |
| 4,474,752 A | 10/1984 | Haslam et al. | |
| 5,410,016 A | 4/1995 | Hubbell et al. | |
| 5,514,380 A | 5/1996 | Song et al. | |
| 5,567,435 A | 10/1996 | Hubbell et al. | |
| 5,702,717 A | 12/1997 | Cha et al. | |
| 5,986,043 A | 11/1999 | Hubbell et al. | |
| 6,004,573 A | 12/1999 | Rathi et al. | |
| 6,060,582 A | 5/2000 | Hubbell et al. | |
| 6,117,949 A | 9/2000 | Rathi et al. | |
| 6,136,333 A * | 10/2000 | Cohn et al. | ......... 424/423 |
| 6,201,072 B1 | 3/2001 | Rathi et al. | |
| 6,451,346 B1 | 9/2002 | Shah et al. | |
| 6,689,803 B2 * | 2/2004 | Hunter | ......... 514/365 |
| 6,841,617 B2 | 1/2005 | Jeong et al. | |
| 7,087,244 B2 | 8/2006 | Jeong et al. | |
| 7,094,810 B2 | 8/2006 | Sant et al. | |
| 7,153,520 B2 | 12/2006 | Seo et al. | |
| 7,179,867 B2 | 2/2007 | Chang et al. | |
| 2004/0219175 A1 | 11/2004 | Kan et al. | |

OTHER PUBLICATIONS

Shim et al, 2005, "pH-induced micellization of biodegradable block copolymers containing sulfamethazine", Macromolecular Research, vol. 13, p. 344-351.*

(Continued)

*Primary Examiner*—Mark Eashoo
*Assistant Examiner*—David Karst
(74) *Attorney, Agent, or Firm*—Lowe Hauptman Ham & Berner, LLP

(57) ABSTRACT

The disclosed is a biodegradable copolymer, an amphiphilic diblock copolymer, composed of a hydrophilic segment and a hydrophobic segment. The hydrophilic segment is an end-capped PEG or derivatives thereof. The hydrophilic segment is a random polymer polymerized of lactone or cyclic $C_3$-$C_6$ molecule and lactic acid/glycolic acid. There is no coupling agent between the hydrophilic and hydrophobic segments, and the biodegradable copolymer is formed by one-pot ring-opening polymerization. The biodegradable copolymer can be dissolved in water to form a thermosensitive material having a phase transfer temperature of 25 to 50° C., thereby being applied to biological activity factor delivery, tissue engineering, cell culture and biological glue.

21 Claims, 26 Drawing Sheets

OTHER PUBLICATIONS

Hyun et al, 2006, "Preparation of diblock copolymers consisting of methoxy poly(ethylene glycol) and poly(epsilon-caprolactone)/poly(L-lactide) and their degradation property", Polymer Engineering and Science, vol. 46, p. 1242-1249.*

Zhang et al, 2006, "Micellization phenomena of amphiphilic block copolymers based on methoxy poly(ethylene glycol) and either crystalline or amorphous poly(caprolactone-b-lactide)", Biomacromolecules, vol. 7, p. 2492-2500.*

Shim et al, 2005, "pH-induced micellization of biodgradable block copolymers containing sulfamethazine", Macromolecular Research, vol. 13, p. 344-351.*

Hyun et al, 2006, "Preparation of diblock copolymers consisting of methoxy poly(ethylene glycol) and poly(epsilon-caprolactone)/polly(L-lactide) and their degradation property", Polymer Engineering and Science, vol. 46, p. 1242-1249.*

Zhang et al, 2006, "Micellization phenomena of amphphilic block copolymers based on methoxy poly(ethylene glycol) and either crystalline or amorphous poly(caprolactone-b-lactide)", Biomacromolecules, vol. 7, p. 2492-2500.*

Jeong et al.; "New biodegradable polymers for injectable drug delivery systems"; Journal of Controlled Release 62; Elsevier; 1999; pp. 109-114.

Kim et al.; "Temperature-responsive and degradable hyaluronic acid/Pluronic composite hydrogels for controlled release of human growth hormone"; Journal of Controlled Release 80; Elsevier; 2002; pp. 69-77.

Lee et al.; "Synthesis and characterization of amphilic poly(2-ehtyl-oxazoline)/ply(E-caprolactone) alternating multiblock copolymers"; Polymer 41; Elsevier; 2000; pp. 7091-7097.

Jeong et al.; "Biodegradable thermoreversible gelling PLGA-g-PEG copolymers"; CHEMCOMM Communication; The Royal Society of Chemistry; Jul. 26, 2001; pp. 1516-1517.

* cited by examiner

BIODEGRADABLE COPOLYMER AND THERMOSENSITIVE MATERIAL

CROSS REFERENCE TO RELATED APPLICATIONS

This Application claims priority of Taiwan Patent Application No. 097111275, filed on Mar. 28, 2008, the entirety of which is incorporated by reference herein. This Application claims priority of Taiwan Patent Application No. 097141336, filed on Oct. 28, 2008, the entirety of which is incorporated by reference herein

BACKGROUND OF THE INVENTION

1. Field of the Invention

The present invention relates to a biodegradable copolymer, and in particular relates to the thermosensitive property of a solution thereof.

2. Description of the Related Art

For hard tissue recovery/surgery, fixation of bone fragments in a comminuted or joint fracture is one of the most challenging procedures. For fixation, a K-pin, a bone nail, or a steel wire may be utilized, however, ablation of soft tissue adhered on the bone fragments is necessary before using the fixation materials. Therefore, blood circulation and bone healing are degraded, and the bone fragments increase risk of destruction into a more powdery form. Commercially available bone cement (e.g. polymethylmethacrylate), serves as an adhesion for bone fragments or a filler for bone cavities. The biological inert bone cement rarely causes allergic reactions and cannot be absorbed by the human body, such that complete bone healing of the bone fragments fixed by the bone cement is difficult. As such, the bone cement is not suitable for fracture caused by trauma. For orthopedist, an absorbable bioadhesion material for bone fragment adhesion to improve bone healing is demanded.

For soft tissue recovery/surgery, an endoscope is utilized for minimal invasive surgery, specially in shoulder reconstructive surgery. Conventional techniques utilize drills to drill a hole through the shoulder bone to seam bone and tendons, thereby consuming time. Recently, sutureless anchors and knotless anchors have been popularly utilized to become mainstream techniques for saving operating time due to inconvenience, and further prevent abrasion and tissue reaction caused from residue knots. If the sutureless anchor is utilized for an ablated tissue, the stress of the anchor will be concentrated on the ablated tissue to form a bulge, such that the bioadhesion is utilized to adhere to the ablated tissues to accelerate tissue regeneration. If the knotless anchor is utilized for the ablated tissue, the healing effect will be dependant upon the operating skill of the surgeon, anchor strength, and degree of tissue regeneration. Meanwhile, the bioadhesion is utilized to adhere to the ablated tissues to improve the healing effect.

For a hip joint, avascular necrosis (AVN) is mainly found in youths and elderly. Although an artificial hip joint can replace a hip joint with AVN, early treatment can also be utilized to cure 75% AVN patients. The present treatment for AVN is core decompression, wherein a hole is drilled from the edge to the front end of the thighbone, and autogenic bone grafts full of veins are implanted into the drilled hole, such that blood is able to flow to the necrosis zone for bone regeneration. However, the described treatment needs an additional operation to collect the autogenic bone grafts from the patient's body, thereby extending the healing period. Note also that a combination of bioadhesion and medicine can be implanted into the thighbone to stimulate veins and bone regeneration following degradation of the bioadhesion to immediately release the medicine.

Meanwhile, delivery of biological activity factors such as medicines, cells, growth factors, and genes are important in biological medicine applications such as medicine therapy, gene therapy, and tissue engineering. The materials which serve as a delivery carrier must possess bio-compatibility and biodegrability for an implanting in vivo. In addition, the material should easily flow in vitro to evenly mix with medicine. The material which is subsequently injected into a body by a catheter or an endoscope, should transform to a gel after injection for fixing activity factors in the predetermined tissue regions, and slowly releasing the activity factors to complete treatment. Presently, a suitable delivery material is rare. Some materials form a gel through chemical reaction, thereby influencing the activity of the biological activity factors or damaging the implanted tissue region. Some materials have excellent thermosensitivity and gel formability but poor biodegradability, thereby preventing applicability for an implantation in vivo.

In U.S. Pat. No. 5,514,380, Song discloses a biodegradable copolymer gel which serves as a medicine delivery matrix. The copolymer is composed of hydrophilic and hydrophobic segments, the hydrophilic segment is primarily polyethyleneoxide (PEO), and the hydrophobic segment is polylactide (PLA), polyglycolide (PGA), polylactide-glycolide (PLGA), or polycaprolactone (PCL). The multi block copolymer is applied to a drug releasing carrier. However, the patent discloses a multi block copolymer such as ABABAB, wherein A means hydrophilic segment and B means hydrophobic segment, without disclosing the thermosensitive property. Furthermore, the patent also fails to disclose that the hydrophobic segment is a random copolymer of lactone or cyclic $C_3$-$C_6$ molecule and lactic acid/glycolic acid.

MacroMed Corporation has four U.S. Pat. No. 5,702,717, No. 6,004,573, U.S. Pat. No. 6,117,949, and U.S. Pat. No. 6,201,072. The patents disclose biodegradable thermosensitive triblock copolymer, such as ABA or BAB. A hydrophilic segment A is a polyethylene glycol (PEG), and a hydrophobic segment B is a polyester. The biodegradable triblock copolymer has a molecular weight of 2000 to 4990 g/mol, and a reverse thermal gelation. The hydrogel, prepared from the copolymer, can be mixed with a medicine at room temperature. The mixture will transform to a gel after being injected into homoiothermic animals, and the medicine release rate is determined by the hydrolysis rate of the gel in vivo. The hydrolysis product of the gel is free of bio-toxicity. However, the patents do not disclose the thermosensitive diblock copolymer AB, and that the hydrophobic segment is a random copolymer of lactone or cyclic $C_3$-$C_6$ molecule and lactic acid/glycolic acid.

In U.S. Pat. Nos. 6,451,346 and 6,004,573, Amgen Corporation discloses ABA and AB block copolymers with pH and thermo sensitivities. The hydrophilic segment A of the copolymer is PEG, and the hydrophilic segment B is PLA or PLGA. However, the patent does not disclose that the hydrophobic segment is a random copolymer of lactone or cyclic $C_3$-$C_6$ molecule and lactic acid/glycolic acid. Furthermore, succinic anhydride is necessary to be a crosslinking agent between the hydrophobic and hydrophilic segments, and is different from the direct ring-opening product of the invention.

In U.S. Pat. No. 7,087,244, Byeongmoon Jeong discloses triblock copolymers such as ABA and BAB with thermosensitivity. The copolymers are applied as a biological activity factor release carrier. However, the patent does not disclose that the hydrophobic segment is a random copolymer of lactone or cyclic $C_3$-$C_6$ molecule and lactic acid/glycolic acid, and the copolymer thereof is triblock not diblock.

In U.S. Pat. Nos. 5,410,016, 5,567,435, and 5,986,043, Hubbell discloses a diblock copolymer AB system. The initiator thereof is a photo initiator or a thermo initiator. In U.S. Pat. No. 5,410,016, the hydrophobic segment B is poly($\alpha$-hydroxy acid) (PHA), poly(glycolic acid) (PGA), PLA, or polylactone such as poly($\epsilon$-caprolactone) (PCL), poly($\delta$-valerolactone) (PVL), or poly($\lambda$-butyrolactone) (PBL). However, the patent does not disclose that the hydrophobic segment is a random copolymer of lactone or cyclic $C_3$-$C_6$ molecule and lactic acid/glycolic acid. Alternatively, in the U.S. Pat. Nos. 5,567,435, and 5,986,043, the diblock copolymer has a PEG center with extension such as PHA, PGA, PLA, polylactone, poly(amino acid), polyanhydride, poly(orthoester), poly(orthocarbonate), or poly(phosphoester). However, similarly, the patents also fail to disclose that the hydrophobic segment is a random copolymer of lactone or cyclic $C_3$-$C_6$ molecule and lactic acid/glycolic acid. In addition, U.S. Pat. No. 6,060,582 discloses a photopolymerized diblock copolymer with three segments B, L, and P. P is an ethylene segment for photo initiation, B is PEG, and L is PHA, acrylic ester monomer or oligomer. The P segment and L segment are first coupled to form a hydrophobic segment, and the hydrophobic segment is then coupled with the B segment. Although the diblock copolymer in U.S. Pat. No. 6,060,582 can be applied for anti-adhesion after surgery, releasing medicine, tissue adhesion, and preventing cell adhesion to tissue, it still fails to disclose that the hydrophobic segment is a random copolymer of lactone or cyclic $C_3$-$C_6$ molecule and lactic acid/glycolic acid.

In U.S. Pat. No. 5,514,380, Samyang Corporation discloses a copolymer with hydrophilic and hydrophobic segments. The hydrophilic segment is PEO and the hydrophobic segment is PLA, PGA, PLGA, or PCL. The copolymer is a thermoplastic biodegradable gel. However, the patent fails to disclose thermosensitivity, and also fails to disclose that the hydrophobic segment is a random copolymer of lactone or cyclic $C_3$-$C_6$ molecule and lactic acid/glycolic acid.

In U.S. Pat. No. 6,136,333, Life Medical Sciences Corporation discloses block copolymers AB and ABA. Segment A is polyester, segment B is polyoxyalkylene polymer unit, segments A and B have a ratio of 1:0.1 to 1:100, and the segments A and B have hexamethylene diisocyanate (HMDI) as crosslinking agent therebetween. The block copolymers serve as anti-adhesion material. However, the patent does not disclose the thermosensitivity, and fails to disclose that the hydrophobic segment is a random copolymer of lactone or cyclic $C_3$-$C_6$ molecule and lactic acid/glycolic acid.

In U.S. Pat. No. 6,841,617, Battle Memorial Institute discloses an An(B) block copolymer that is a thermosensitive and biodegradable gel, wherein A is PEG and B is polyester. However, the polymerization thereof is through grafting, and it also fails to disclose that the hydrophobic segment is a random copolymer of lactone or cyclic $C_3$-$C_6$ molecule and lactic acid/glycolic acid.

In U.S. Pat. No. 7,094,810, Lapopharm Corporation discloses a block copolymer AB. The hydrophilic segment A is PEO, and an the hydrophobic segment B is poly(butyl(alkyl) acrylate-co-(alkyl)acrylic acid. However, the patent fails to disclose that the hydrophobic segment is a random copolymer of lactone or cyclic $C_3$-$C_6$ molecule and lactic acid/glycolic acid.

In U.S. Pat. No. 7,153,520, Samyang Corporation discloses an amphiphilic diblock copolymer that is a slow-degradable drug delivery material, wherein the hydrophilic segment is PEG, and hydrophobic is PLA, PCL, PLGA, PLDO, poly(lactide-co-p-dioxanone), poly(orthoester), polyanhydride, poly(amino acid), and polycarbonate. However, the patent does not disclose that the copolymer is thermosensitive.

In U.S. Pat. No. 4,188,373, Krezanoski discloses an aqueous solution PEO-PPO polymer with a phase transfer temperature of 25° C. to 40° C., wherein the hydrogel system can be applied as a drug delivery carrier. However, the polymer material thereof has no hydrophobic segment.

In U.S. Pat. No. 4,474,752, Haslam discloses a medicine delivery system, wherein the medicine is liquid at room temperature and transforms to a semisolid or gel at body temperature. The hydrogel has 40-80% PEO and 20-60% PPO and a molecular weight of 7,000 to 50,000. However, the hydrogel does not have a hydrophobic segment.

In the *Chem. Commun.* 2001, 1516-1517, Jeong discloses a thermosensitive copolymer PLGA-g-PEG. The backbone of the polymer is PLGA and the side chains PEG are grafted on the backbone, wherein the lactide, glycolic acid, and PEG have a molar ratio of 3.2:1:2.8. The copolymer has a molecular weight of 9,300, a weight percent in water of 25 wt %, and a phase transfer temperature of 30° C. However, the paper fails to disclose that the hydrophobic segment is a random copolymer of lactone or cyclic $C_3$-$C_6$ molecule and lactic acid/glycolic acid.

In the *Polymer* 2000, 41, 7091-7097, Lee discloses an amphiphilic polymer material with thermosensitivity. The polymer material is copolymerized of 2-ethyl-2-oxazoline and $\epsilon$-caprolactone. However, the paper does not disclose that the hydrophobic segment is a random copolymer of lactone or cyclic $C_3$-$C_6$ molecule and lactic acid/glycolic acid.

In the *Journal of Controlled Release* 2002, 80, 69-77, Kim discloses a thermosensitive composite polymer hydrogel, wherein the hydrogel is photopolymerized of polyethylene oxide-polypropylene oxide and hyaluronic acid. The hydrogel serves as a human growth hormone delivery carrier to study drug release kinetics of related medicines and proteins. However, the polymer hydrogel does not have a hydrophobic segment.

In 1999, You Han Bae utilized condensation of PEG and PLA with carboxylic acid terminals to obtain a thermosensitive block copolymer PLA-PEG-PLA. The PEG has a molecular weight (Mn) of 1,000 to 2,000, and the PLA has a molecular weight of 820 to 3,150. The 1 wt % PLA-PEG-PLA aqueous solution has a low critical solution temperature (LCST) of 27° C. to 45° C., the aqueous solution does not transform into a gel or a semisolid, and the LCST is modified by tuning the length of the hydrophobic segment PLA. However, the thermosensitive polymer is not a diblock copolymer, and the hydrophobic segments thereof were not random copolymers of lactone or cyclic $C_3$-$C_6$ molecule and lactic acid/glycolic acid.

BRIEF SUMMARY OF THE INVENTION

The invention discloses a biodegradable copolymer, having a general formula: A-B; wherein A is a hydrophilic segment, having a general formula:

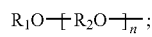

$R_1$ is $C_{1-8}$ alkyl; $R_2$ is ethyl, $C_{1-8}$ alkyl ethyl, $C_{1-8}$ alkoxyl ethyl, or combinations thereof; and n is an integral of 5-20; and B is a hydrophobic segment, having a general formula:

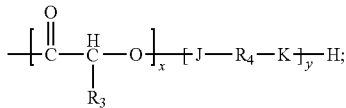

$R_3$ is hydrogen or methyl; $R_4$ is a linear, branched or cyclic, saturated or unsaturated $C_2$-$C_5$ alkanediyl group optionally comprising one or more hetero atoms including O, S or N; J is C=O, C=S, C—CHO, C=NH, or C=NR$_5$, wherein $R_5$ is $C_1$-$C_3$ alkyl group; K is O, S, C—CHO, NH, or NR$_6$, wherein $R_6$ is $C_1$-$C_3$ alkyl group; x is an integral of 5-20; and y is an integral of 5-20.

The invention also provides a thermosensitive material, comprising water and the biodegradable copolymer as described above dissolved in the water to form a solution, wherein the hydrophobic segment B aggregates to form micelles.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
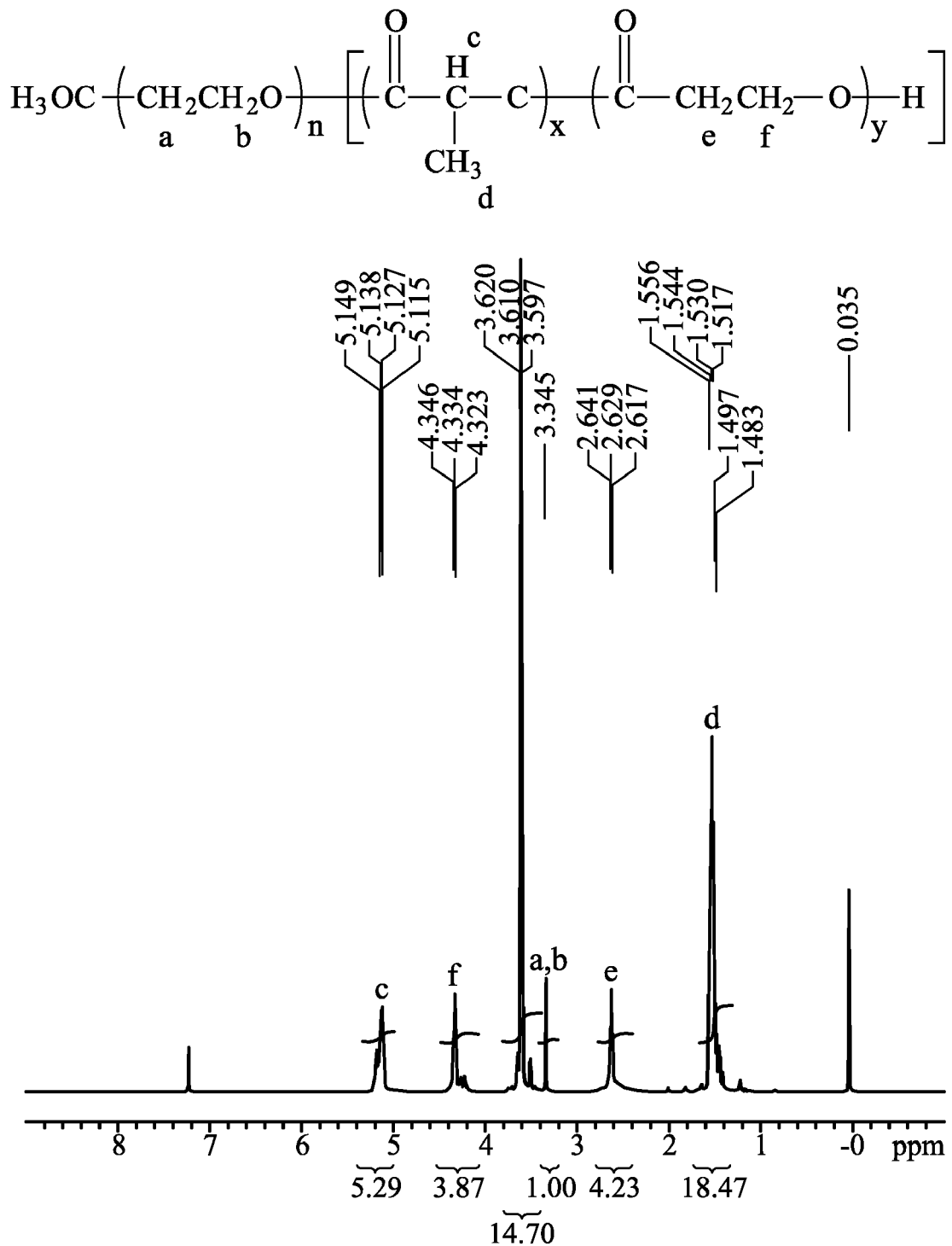
FIG. 1 is an NMR spectrum of mPEG-PPLA in one example of the invention.

The following description is of the best-contemplated mode of carrying out the invention. This description is made for the purpose of illustrating the general principles of the invention and should not be taken in a limiting sense. The scope of the invention is best determined by reference to the appended claims.

The invention discloses a biodegradable copolymer having a general formula as shown in Formula 1. The hydrophilic segment A has a general formula as shown in Formula 2. In Formula 2, $R_1$ is $C_{1-8}$ alkyl. $R_2$ is ethyl, $C_{1-8}$ alkyl ethyl, $C_{1-8}$ alkoxyl ethyl, or combinations thereof. n is an integral of 5-20. The hydrophobic segment B has a general formula as shown in Formula 3. In Formula 3, $R_3$ is hydrogen or methyl. $R_4$ is a linear, branched or cyclic, saturated or unsaturated $C_2$-$C_5$ alkanediyl group; this alkanediyl group can optionally be interrupted by one or more hetero atoms such as O, S or N. J is C=O, C=S, C—CHO, C=NH, or C=NR$_5$, wherein $R_5$ is $C_1$-$C_3$ alkyl group. K is O, S, C—CHO, NH, or NR$_6$, wherein $R_6$ is $C_1$-$C_3$ alkyl group. x is an integral of 5-20. y is an integral of 5-20.

A-B (Formula 1)

$R_1O\!\!-\!\!\!\!\!-\!\!\!\!-\!\!(R_2O\!\!-\!\!\!\!\!-\!\!\!\!-)_n$ (Formula 2)

(Formula 3)

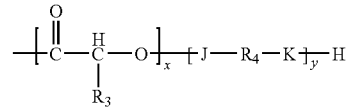

Manufacturing of the biodegradable copolymer is described as below. First, since an equivalent ratio of alcohol and ethylene glycol or derivative thereof is reacted under an acid condition, therefore one terminal of the ethylene glycol is endcapped by an alkoxy group. In one embodiment, the ethylene glycol derivative can be a $C_{1-8}$ alkyl ethylene glycol such as methyl ethylene glycol, or a $C_{1-8}$ alkoxy ethylene glycol such as methoxy ethylene glycol. The alcohol is $C_{1-8}$ alcohol. In one embodiment, the alcohol is methanol. In one embodiment, the methoxy endcapped poly ethylene glycol, the hydrophilic segment of the biodegradable copolymer, has a molecular weight of 300 to 1000.

Next, lactic acid, glycolic acid, or the precursors thereof are selected as a necessary monomer of the hydrophobic segment. The lactic acid can be any type of enantiomers or mixtures thereof, such as D-lactic acid, L-lactic acid, or DL-lactic acid. The lactic acid precursor can be lactide of any type of enantiomers or mixtures thereof, such as D-lactide, L-lactide, or DL-lactide. The lactide has a general formula as shown in Formula 4. The glycolic acid precursor includes glycolide as shown in Formula 5.

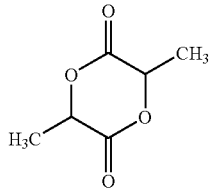

(Formula 4)

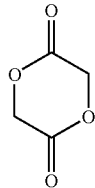

(Formula 5)

In addition, the lactone or the cyclic $C_3$-$C_6$ molecule can be selected as one necessary monomer of the hydrophobic segment. Suitable lactones includes β-propiolactone, γ-thiobutyrolactone, δ-valerolactone, or ε-caprolactone. Suitable cyclic $C_3$-$C_6$ molecule includes 2-Iminothiolane hydrochloride(2-IT), (4R)-(−)-2-Thioxo-4-thiazolidinecarboxylic acid, (−)-2-Oxo-4-thiazolidinecarboxylic acid, DL-N-Acetylhomocysteine thiolactone, 5-Thiazolecarboxaldehyde, γ-butyrolactam, or 1-Methyl-2-pyrrolidinone (NMP).

Subsequently, the endcapped polyethylene glycol or derivatives thereof, lactic acid and/or glycolic acid and precursor thereof, lactone, or cyclic $C_3$-$C_6$ molecule are mixed and reacted to form a diblock copolymer by ring-opening polymerization. The copolymer is a biodegradable material, the hydrophilic segment is endcapped polyethylene glycol or derivatives thereof, and the hydrophobic segment is copolymerized of lactic acid/glycolic acid (or derivatives thereof), lactone, or cyclic $C_3$-$C_6$ molecule. In one embodiment, the lactic acid/glycolic acid molar ratio (x in Formula 3) is greater than or equal to the lactone or cyclic $C_3$-$C_6$ molecule molar ratio (y in formula 3). In one embodiment, the lactic acid/glycolic acid and the lactone or cyclic $C_3$-$C_6$ molecule have a molar ratio (x:y) between 50:50 to 90:10.

Because the manufacturing of the biodegradable polymer of the invention is by one-pot reaction without any additional crosslinking agent or coupling agent between the hydrophilic and hydrophobic segments, synthesis periods and steps are reduced.

The described biodegradable copolymer is further dissolved in water to form a thermosensitive material, so that properties may be measured, e.g. critical micelle concentration, micelle diameter, gelling time, hemolysis, adhesion strength, and drug release. In one embodiment, the biodegradable copolymer and water have a weight ratio of 2:98 to 40:60. In another embodiment, the biodegradable copolymer and water have a weight ratio of 15:85 to 30:70. If the weight ratio is less than 2:98, the solution cannot be gelled. On the other hand, the biodegradable copolymer cannot be totally dissolved in water if the weight ratio is greater than 40:60 or 30:70. As known from invention experiments, the critical micelle concentration of the solution is about 0.003 wt % to 0.07 wt % with a micelle diameter of 5 nm to 500 nm. In one embodiment, the described thermosensitive material has a phase transfer temperature of 25° C. to 50° C. In one embodiment, the described thermosensitive material has a phase transfer temperature of 30° C. to 40° C. The thermosensitive material is liquid when the temperature is lower than the phase transfer temperature, and forms a hydrogel when the temperature is higher than the phase transfer temperature. According to the measurement, the gelling time of the thermosensitive material is less than 30 seconds. The hydrogel has excellent adhesion strength, non-hemolysis, and high biocompatibility. The phase transfer is reversible, meaning that the hydrogel will return to a liquid phase if the temperature is reduced to lower than the phase transfer temperature. In addition, the hydrophobic segment of the copolymer can be hydrolysis to a harmless compound for a human body. The hydrophilic segment of the copolymer can be dissolved in water and then egested by human body. In drug release experiments, the thermosensitive material of the invention releases drug in different ratios corresponding to the concentration thereof, and it can be applied as a long-acting medicine carrier. Accordingly, the thermosensitive material can be applied to biological activity factor delivery, tissue engineering, cell culture, or biological glue, wherein the biological activity factor includes medicine, cell, growth factor, inorganic salt, ceramic material, poly-(amino acid), peptide, protein, gene, DNA sequence or RNA sequence. The biological glue is applied in a cell organism, tissue, implant surface adhesion, soft and hard tissue recovery, or an implant carrier filler, or a hemostatic glue. The thermosensitive material type may be applied through injection, pastille, powder, gel, solution, or oral liquid

EXAMPLES AND COMPARATIVE EXAMPLES

Example 1

Copolymer of Methoxy Endcapped Polyethylene Glycol and Lactide/β-Propiolactone Random Copolymer, Hereinafter mPEG-PPLA 21.14 g of methoxy endcapped polyethylene glycol (mPEG, Molecular weight is 550 g/mol), 50 g of lactide, and 18.77 g of β-propiolactone were subsequently charged in an anhydrous reactor, and the reactor temperature was slowly increased until the substances were totally dissolved. The temperature was continuously increased to 160° C., and 42.0 μL stannous catalyst (stannous 2-ethylhexanoate) was added in the reactor to process polymerization at 160° C. for 8 hours. The reaction is shown in Formula 6. The reaction result was precipitated in ethyl ether/hexane (volume ratio is 1:9) as a semitransparent gel. The semitransparent gel was washed three times to remove monomers and then dried in a vacuum at 40° C. for 24 hours to obtain product mPEG-PPLA.

(Formula 6)

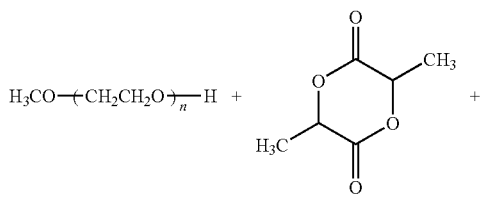

-continued

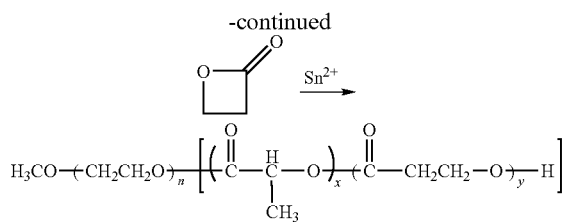

Figure 2:
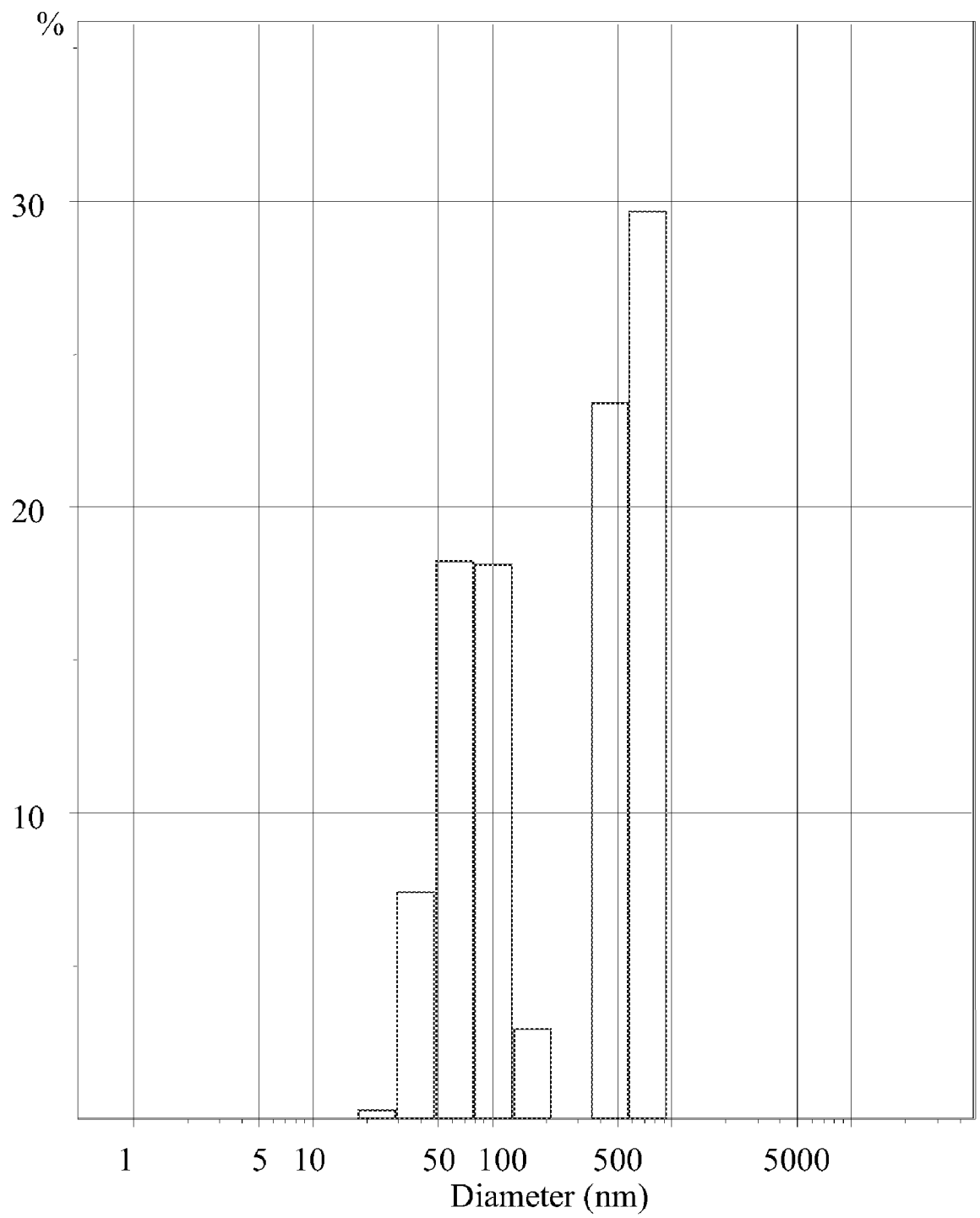
FIG. 2 is a micelle diameter distribution diagram of mPEG-PPLA in one example of the invention.
Figure 3:
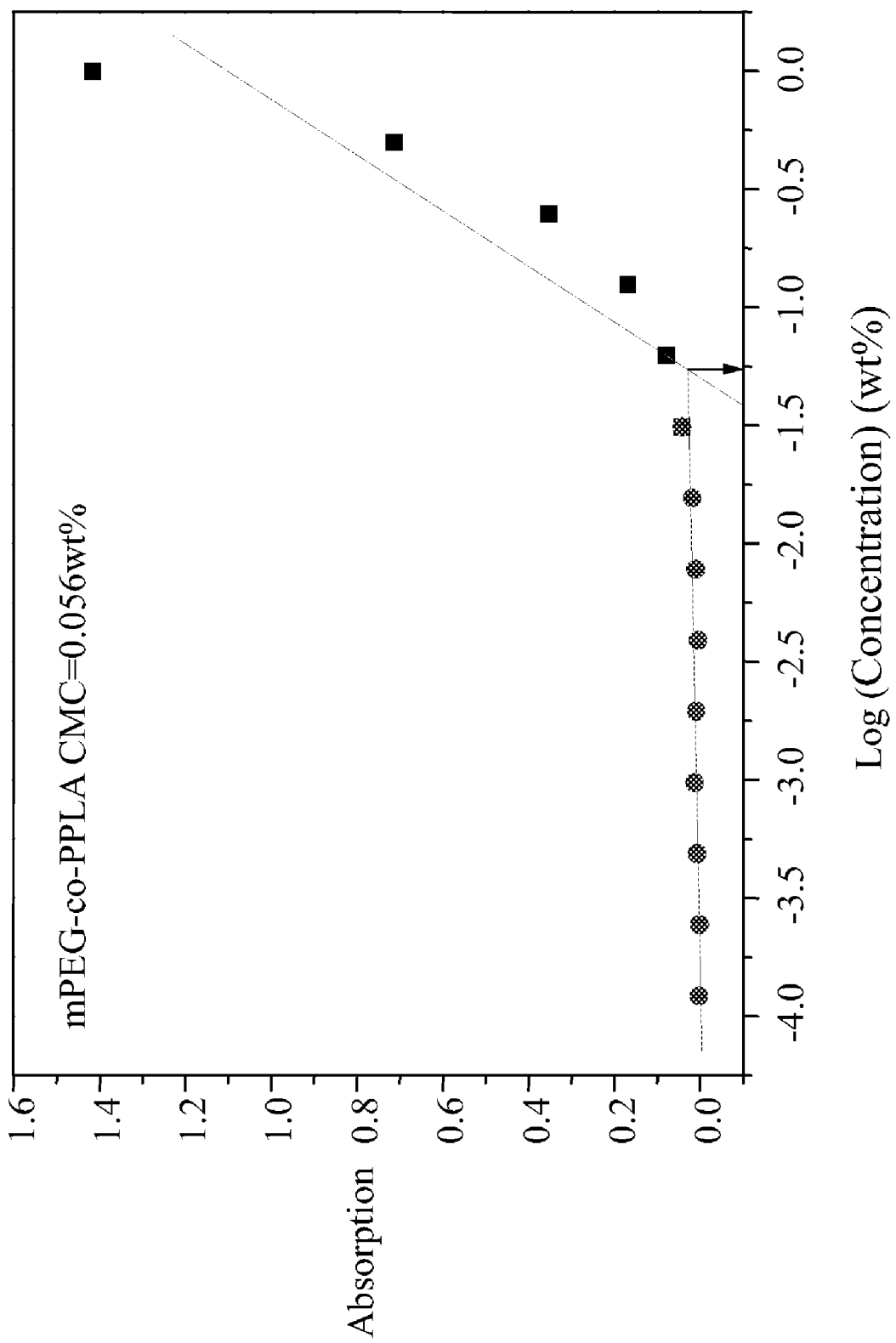
FIG. 3 is a critical micelle concentration diagram of mPEG-PPLA in one example of the invention.
Figure 4:
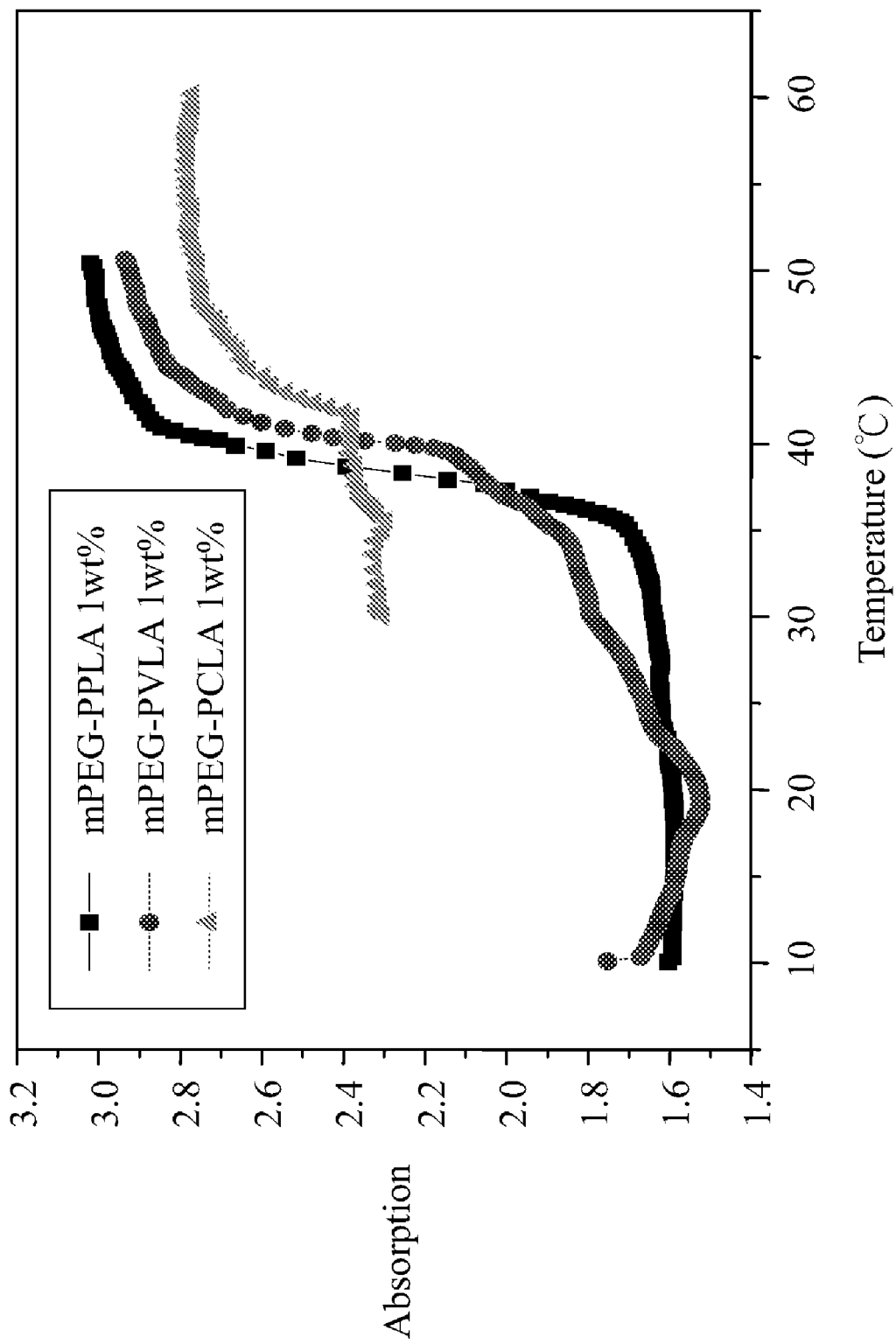
FIG. 4 is a UV transmittance versus temperature diagram of mPEG-PPLA, mPEG-PVLA, and mPEG-PCLA in examples of the invention.
Figure 5:
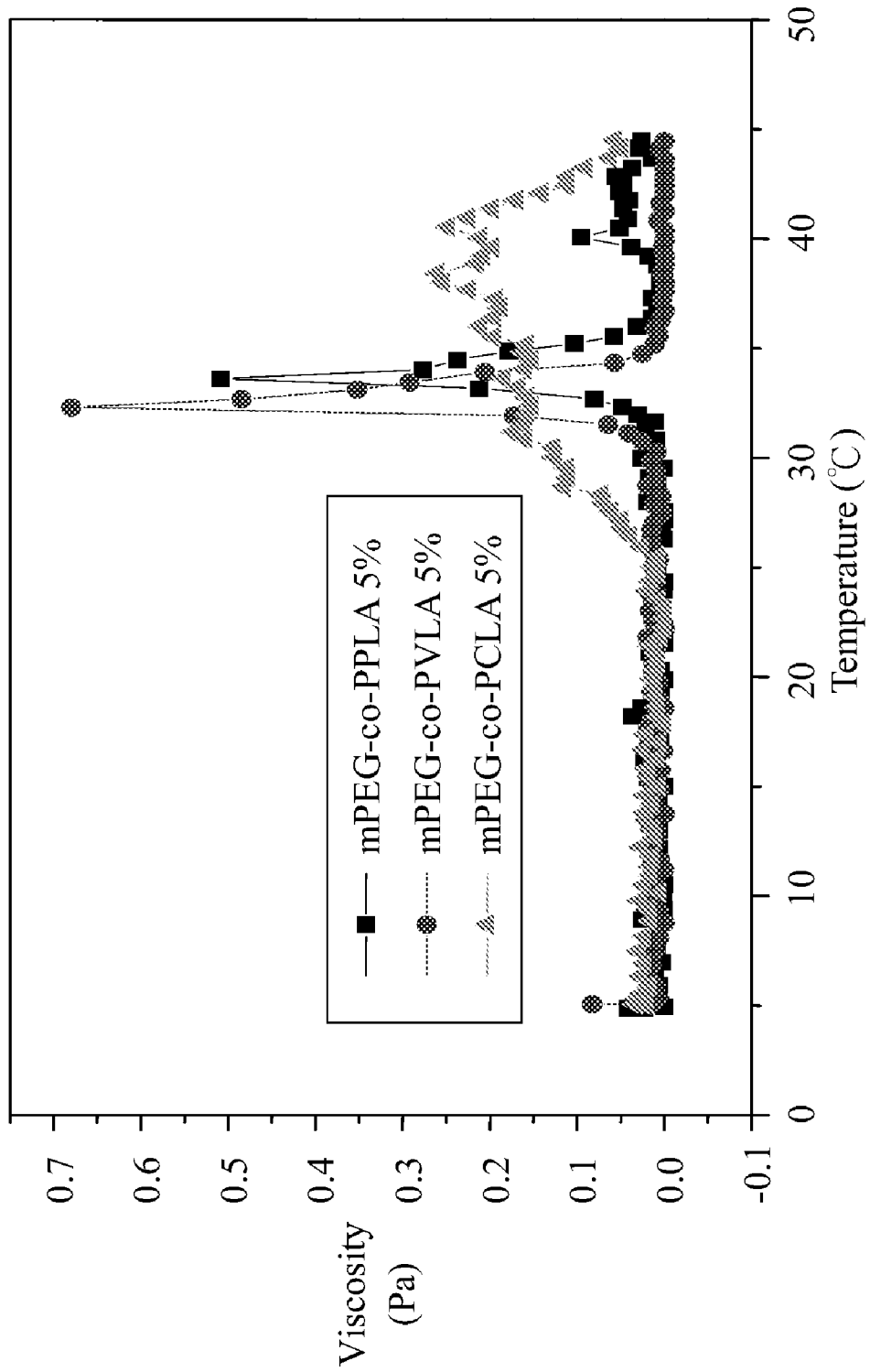
FIG. 5 is a viscosity versus temperature diagram of mPEG-PPLA, mPEG-PVLA, and mPEG-PCLA in examples of the invention.

The copolymer mPEG-PPLA had an NMR spectrum as shown in FIG. 1, and a diameter analysis with instrument Zetasizer 1000H as shown in FIG. 2. The mPEG-PPLA dissolved in water is the thermosensitive material of the invention, and the critical micelle concentration analysis is shown in FIG. 3, the UV transmittance related to temperature is shown in FIG. 4, and the viscosity related to temperature is shown in FIG. 5. When the mPEG-PPLA liquid transforms to hydrogel, its UV transmittance was reduced. The thermosensitive material was a flowable transparent solution at a low temperature, a semitransparent solution with higher viscosity at 25° C., and a non-flowable opaque hydrogel at 40° C. The gelling time of the mPEG-PPLA at 37° C. measured in a water sink was about 27.2 seconds. The hydrogel had adhesion strength of 52 gf/mm$^2$, which is better than that of a commercially available fibrin glue (about 49 gf/mm$^2$).

Example 2

Copolymer of Methoxy Endcapped Polyethylene Glycol and Lactide/δ-Valerolactone Random Copolymer, Hereinafter mPEG-PVLA 17.03 g of methoxy endcapped polyethylene glycol (mPEG, Molecular weight is 550 g/mol), 33.6 g of lactide, and 10.0 g of δ-valerolactone were subsequently charged in an anhydrous reactor, and the reactor temperature was slowly increased until the substances were totally dissolved. The temperature was continuously increased to 160° C., and 34.0 μL stannous catalyst (stannous 2-ethylhexanoate) was added in the reactor to process polymerization at 160° C. for 8 hours. The reaction is shown in Formula 7. The reaction result was precipitated in ethyl ether/hexane (volume ratio is 1:9) as a semitransparent gel. The semitransparent gel was washed three times to remove monomers and then dried in vacuum at 40° C. for 24 hours to obtain product mPEG-PVLA.

(Formula 7)

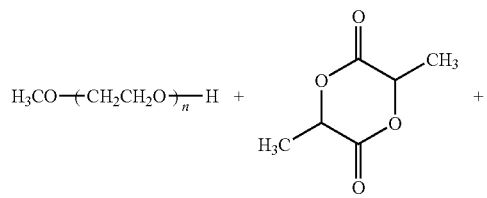

-continued

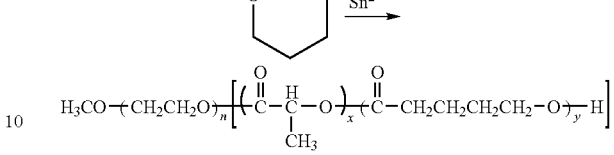

Figure 6:
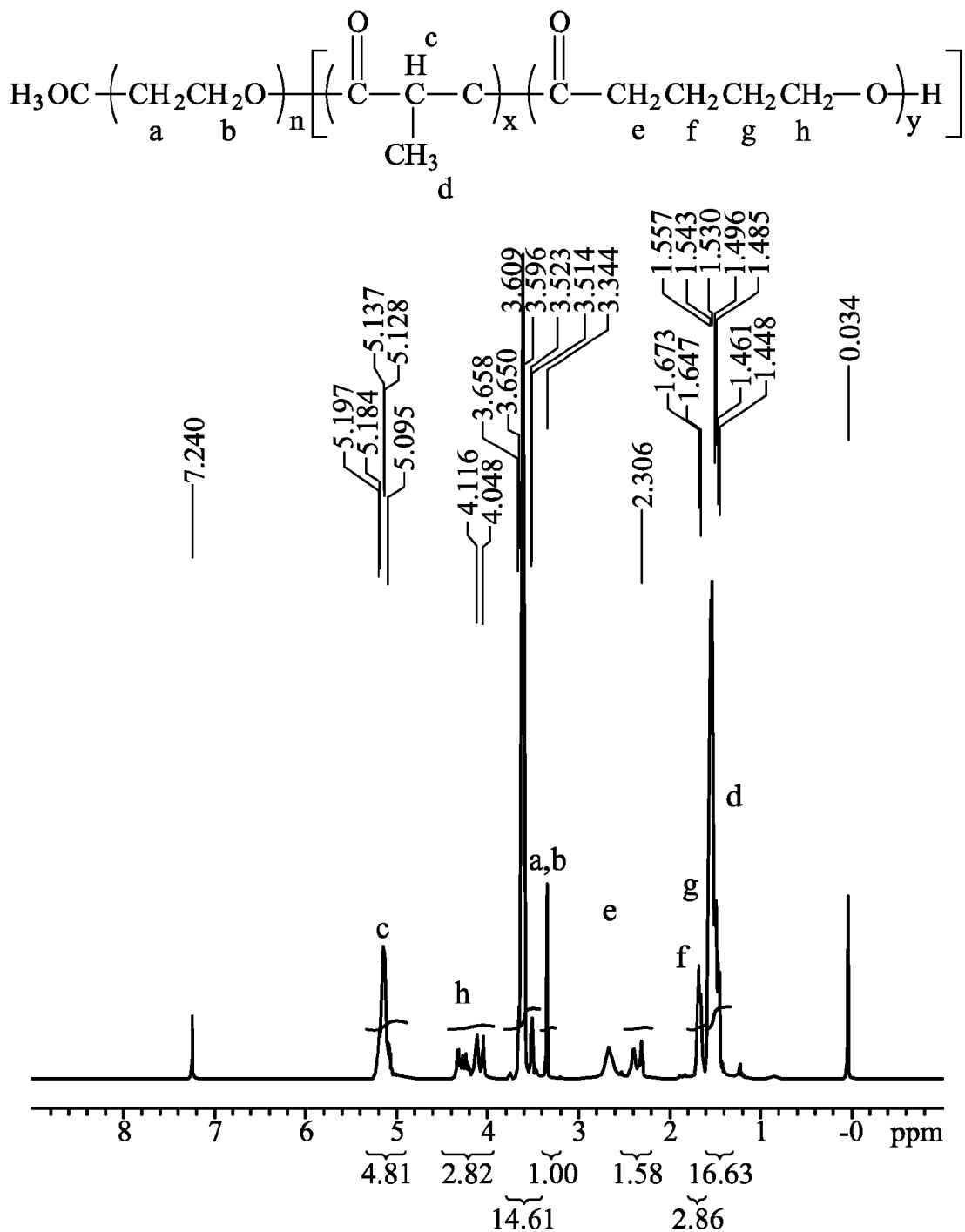
FIG. 6 is an NMR spectrum of mPEG-PVLA in one example of the invention.
Figure 7:
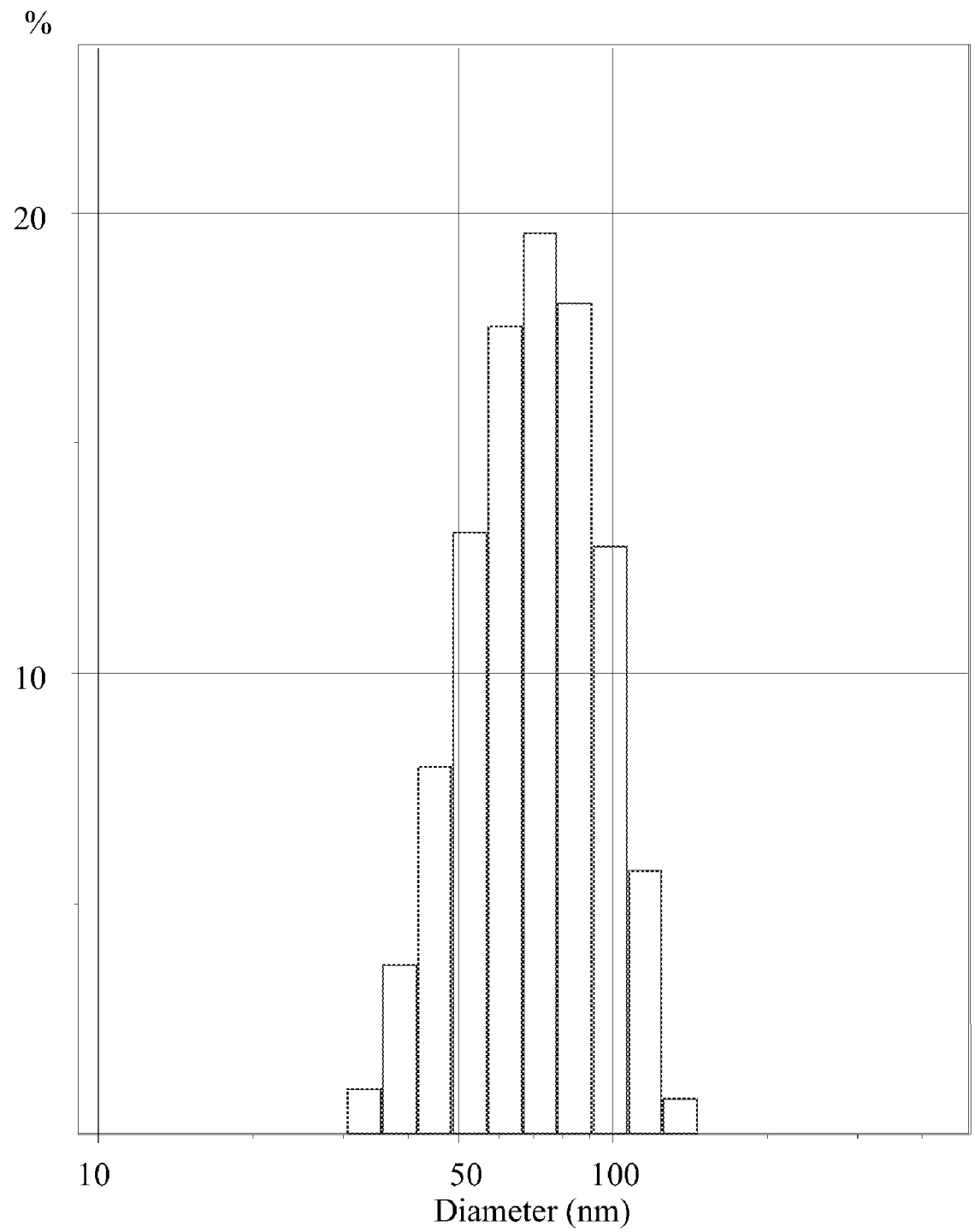
FIG. 7 is a micelle diameter distribution diagram of mPEG-PVLA in one example of the invention.
Figure 8:
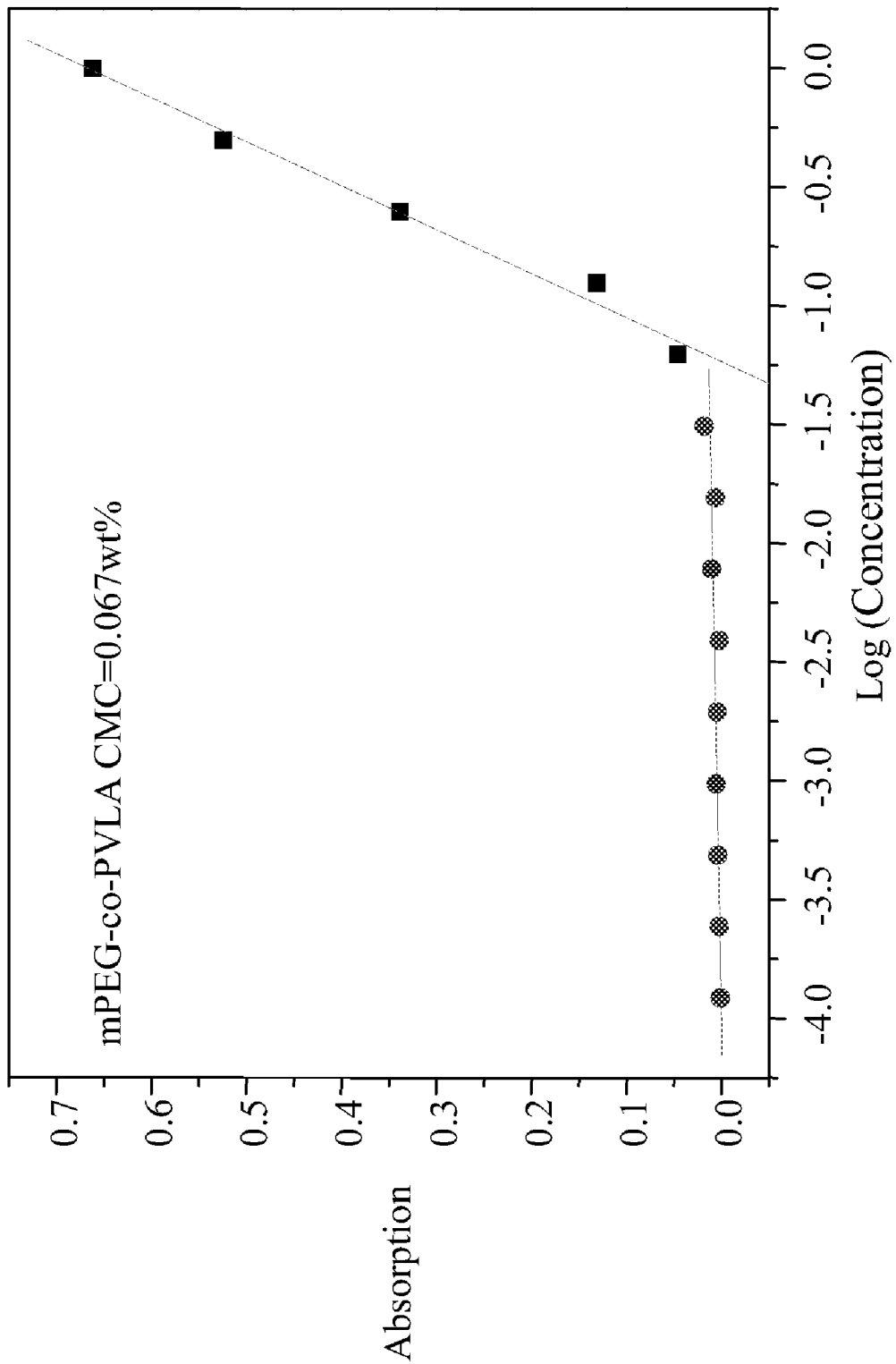
FIG. 8 is a critical micelle concentration diagram of mPEG-PVLA in one example of the invention.
Figure 9:
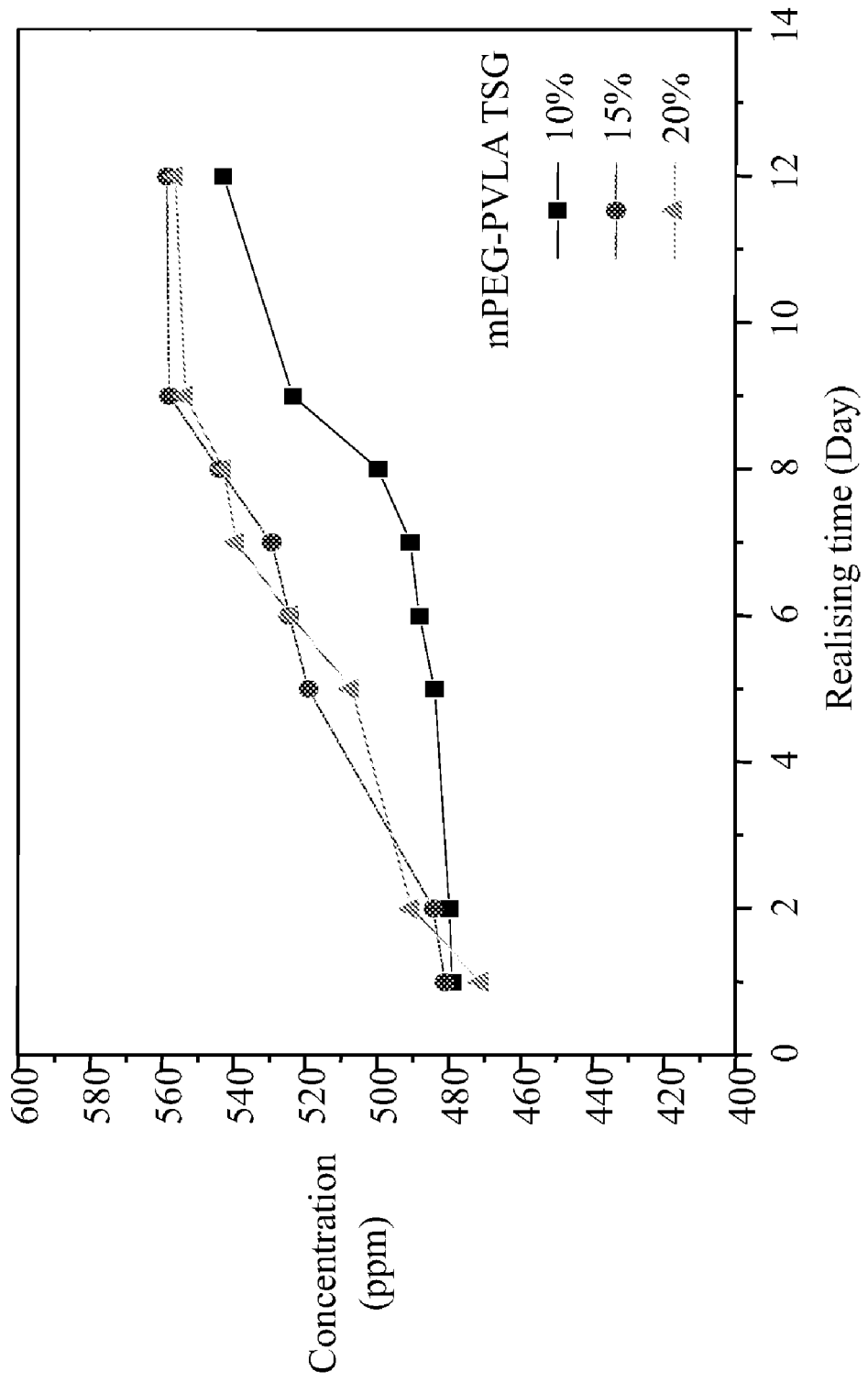
FIG. 9 is a medicine release curve of cyclosporine corresponding to different concentrations of mPEG-PVLA solution in one example of the invention.

The copolymer mPEG-PVLA has an NMR spectrum as shown in FIG. 6, and a diameter analysis with instrument Zetasizer 1000H as shown in FIG. 7. The mPEG-PVLA dissolved in water is the thermosensitive material of the invention, the critical micelle concentration analysis is shown in FIG. 8, the UV transmittance related to temperature is shown in FIG. 4, and the viscosity related to temperature is shown in FIG. 5. When the mPEG-PVLA liquid transformed to hydrogel, its UV transmittance was reduced. The thermosensitive material was a flowable transparent solution at a low temperature, a semi-transparent solution with higher viscosity at 25° C., and a non-flowable opaque hydrogel at 40° C. The gelling time of the mPEG-PVLA at 37° C. measured in a water sink was about 27.5 seconds. The hydrogel had adhesion strength of 58 gf/mm$^2$, which is better than that of commercially available fibrin glue (about 49 gf/mm$^2$). The medicine release experiment of cyclosporine corresponding to different concentrations of mPEG-PVLA solution is shown in FIG. 9. The thermosensitive material mPEG-PVLA solution is suitable for biological activity factor delivery such as medicine release.

Example 3

Copolymer of Methoxy Endcapped Polyethylene Glycol and Lactide/ε-Caprolactone Random Copolymer, Hereinafter mPEG-PCLA 17.62 g of methoxy endcapped polyethylene glycol (mPEG, Molecular weight is 550 g/mol), 33.6 g of lactide, and 11.4 g of ε-caprolactone were subsequently charged in an anhydrous reactor, and the reactor temperature was slowly increased until the substances were totally dissolved. The temperature was continuously increased to 160° C., and 35.0 μL stannous catalyst (stannous 2-ethylhexanoate) was added in the reactor to process polymerization at 160° C. for 8 hours. The reaction is shown in Formula 8. The reaction result was precipitated in ethyl ether/hexane (volume ratio is 1:9) as a semitransparent gel. The semitransparent gel was washed three times to remove monomers and then dried in vacuum at 40° C. for 24 hours to obtain product mPEG-PCLA.

(Formula 8)

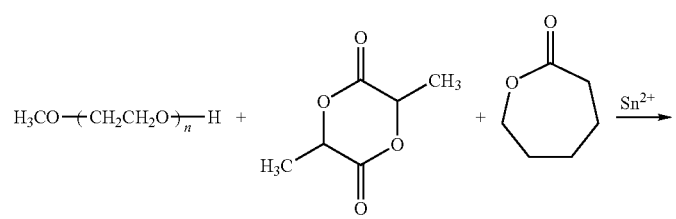

-continued

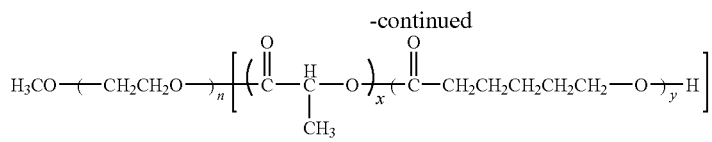

Figure 10:
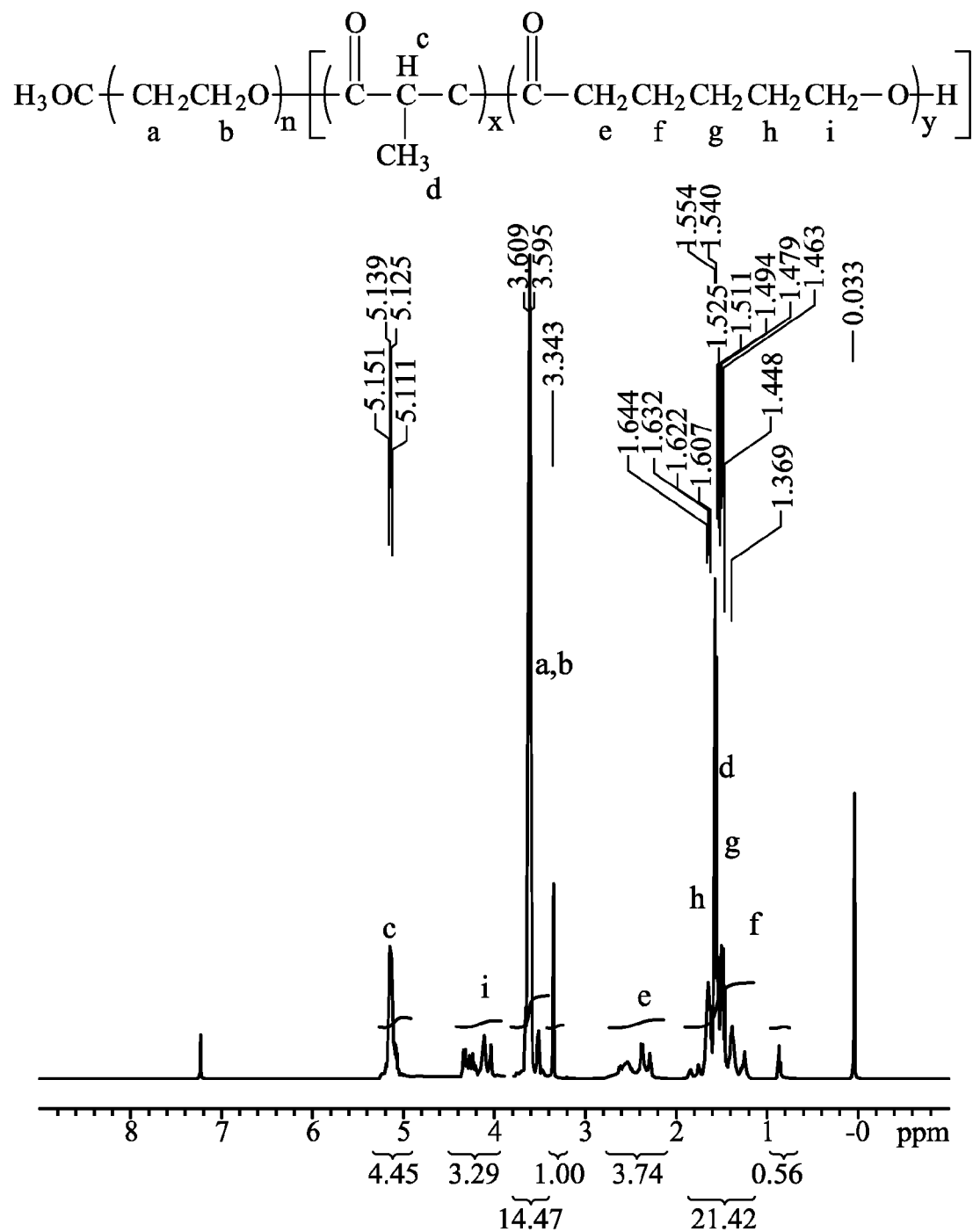
FIG. 10 is an NMR spectrum of mPEG-PCLA in one example of the invention.
Figure 11:
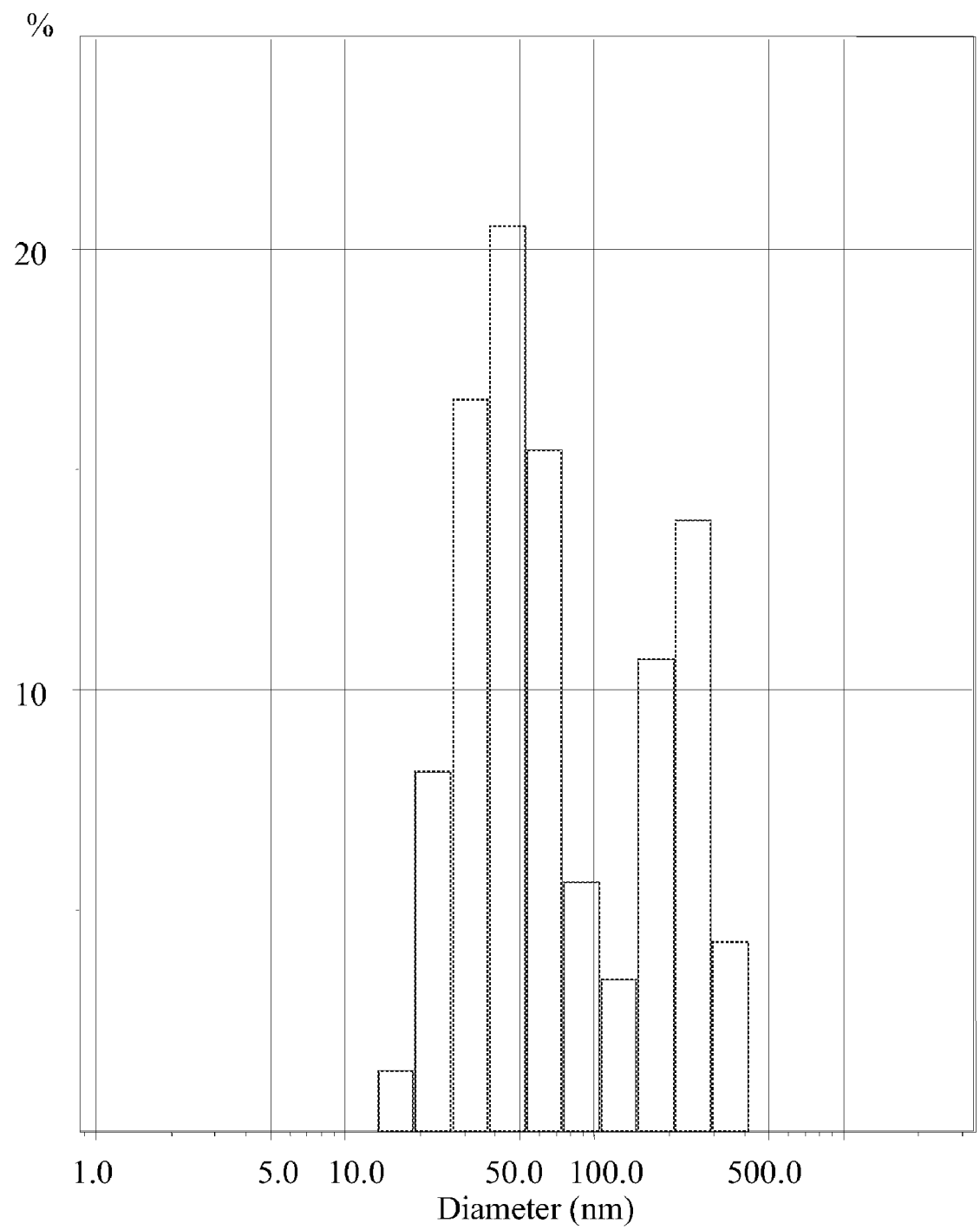
FIG. 11 is a micelle diameter distribution diagram of mPEG-PCLA in one example of the invention.
Figure 12:
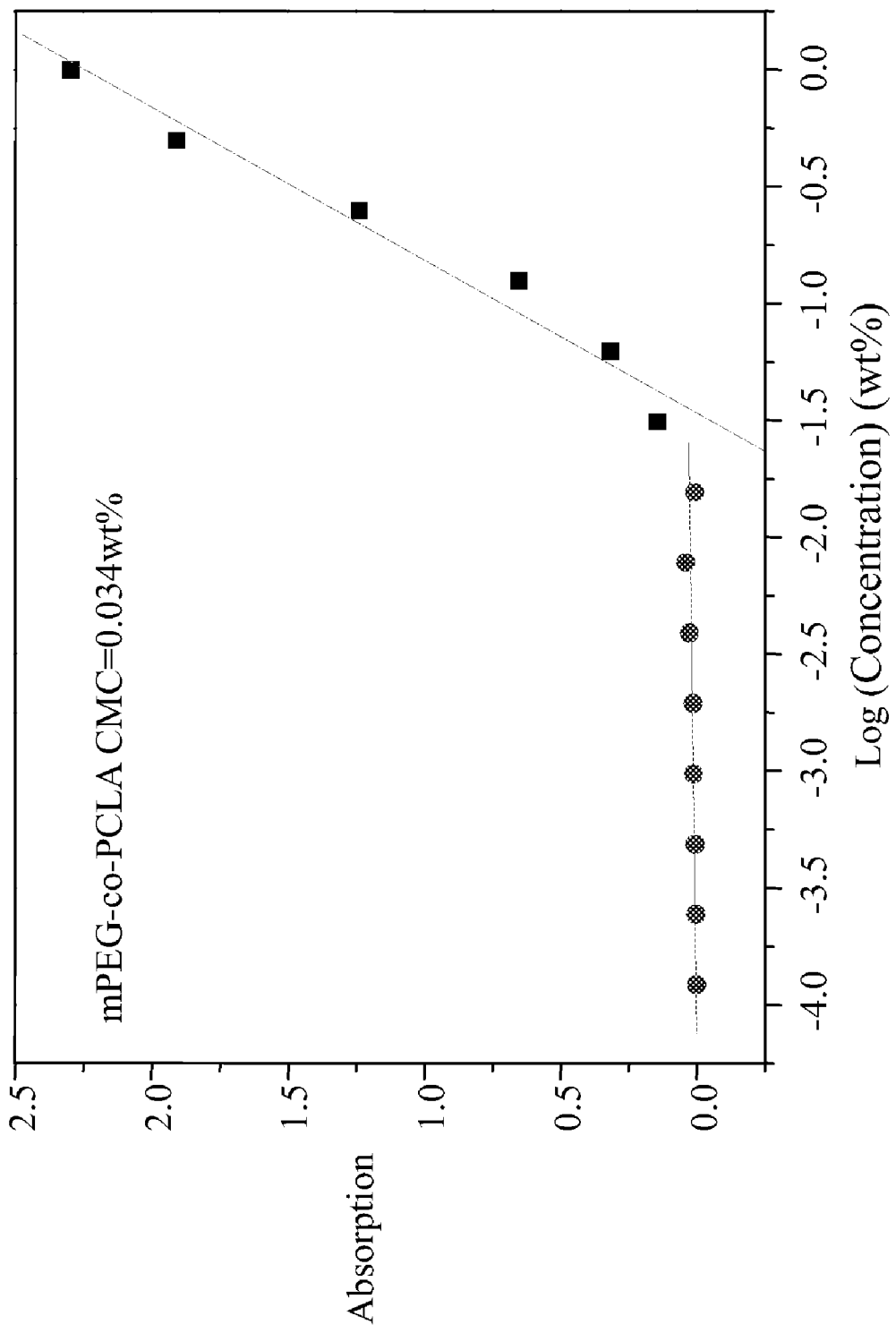
FIG. 12 is a critical micelle concentration diagram of mPEG-PCLA in one example of the invention.
Figure 13:
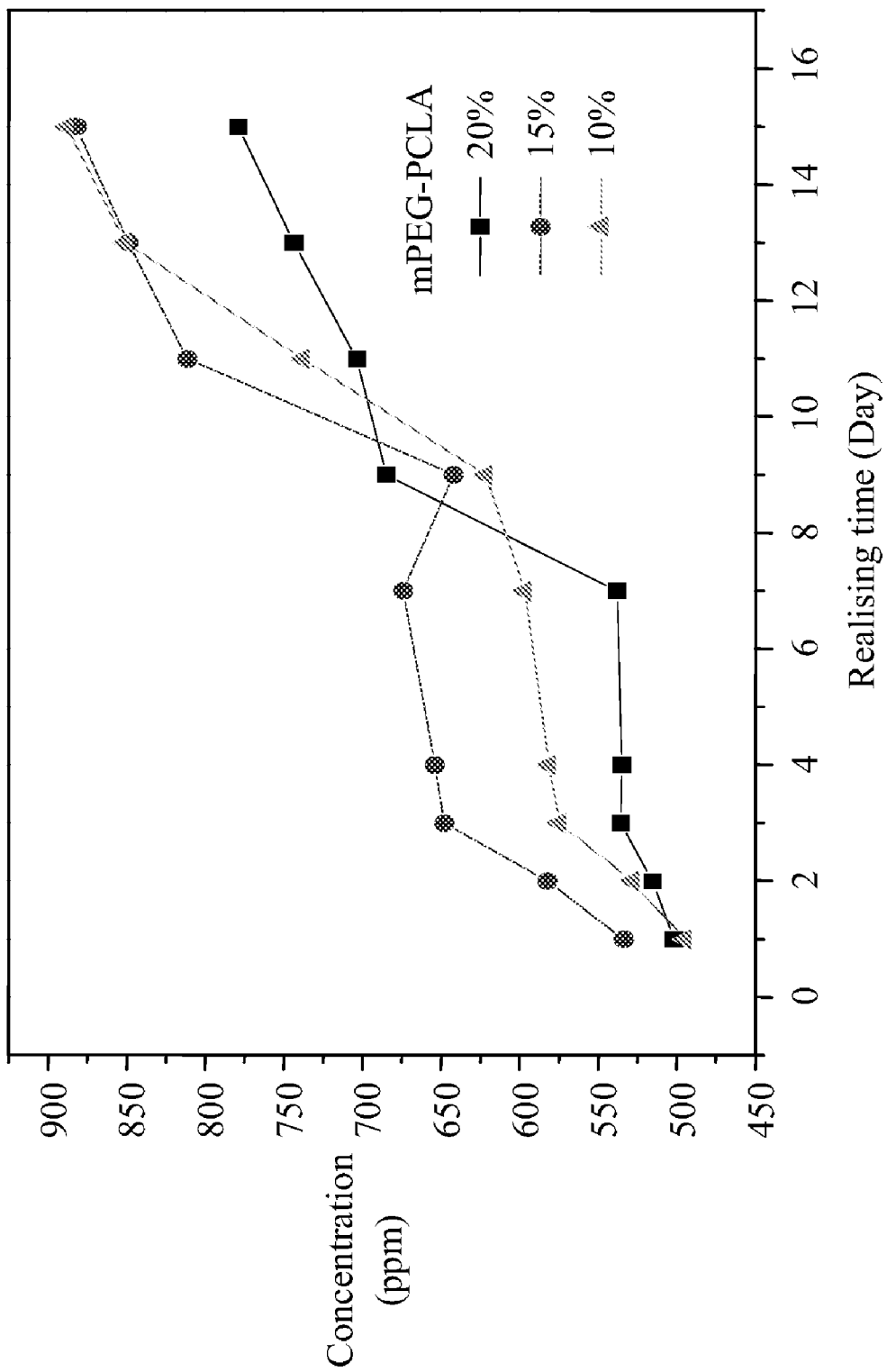
FIG. 13 is a medicine release curve of cyclosporine corresponding to different concentrations of mPEG-PCLA solution in one example of the invention.

The copolymer mPEG-PCLA had an NMR spectrum as shown in FIG. 10, and a diameter analysis with instrument Zetasizer 1000H as shown in FIG. 11. The mPEG-PCLA dissolved in water is the thermosensitive material of the invention, the critical micelle concentration analysis is shown in FIG. 12, the UV transmittance related to temperature is shown in FIG. 4, and the viscosity related to temperature is shown in FIG. 5. When the mPEG-PCLA liquid transformed to hydrogel, its UV transmittance was reduced. The thermosensitive material was a flowable transparent solution at a low temperature, a semi-transparent solution with higher viscosity at 25° C., and a non-flowable opaque hydrogel at 40° C. The gelling time of the mPEG-PCLA at 37° C. measured in a water sink was about 29.2 seconds. The hydrogel had adhesion strength of 100 gf/mm$^2$, which is better than that of commercially available fibrin glue (about 49 gf/mm$^2$). The medicine release experiment of cyclosporine corresponding to different concentrations of mPEG-PCLA solution is shown in FIG. 13. The thermosensitive material mPEG-PCLA solution is suitable for biological activity factor delivery such as medicine release.

Example 4

Copolymer of Methoxy Endcapped Polyethylene Glycol and Lactide/γ-Thiobutyrolactone Random Copolymer, Hereinafter mPEG-PSLA 18.43 g of methoxy endcapped polyethylene glycol (mPEG, Molecular weight is 550 g/mol), 40 g of lactide, and 7.083 g of γ-thiobutyrolactone were subsequently charged in an anhydrous reactor, and the reactor temperature was slowly increased until the substances were totally dissolved. The temperature was continuously increased to 160° C., and 26.026 μL stannous catalyst (stannous 2-ethylhexanoate) was added in the reactor to process polymerization at 160° C. for 8 hours. The reaction is shown in Formula 9. The reaction result was precipitated in ethyl ether/hexane (volume ratio is 1:9) as a semitransparent gel. The semitransparent gel was washed three times to remove monomers and then dried in vacuum at 40° C. for 24 hours to obtain product mPEG-PSLA.

(Formula 9)

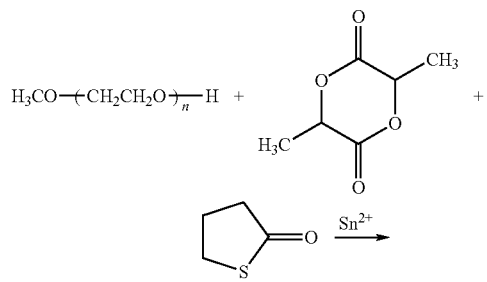

-continued

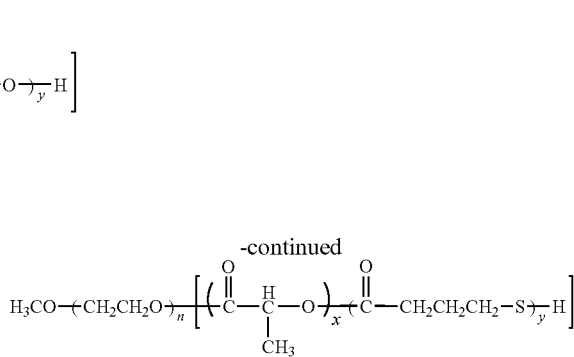

Figure 14:
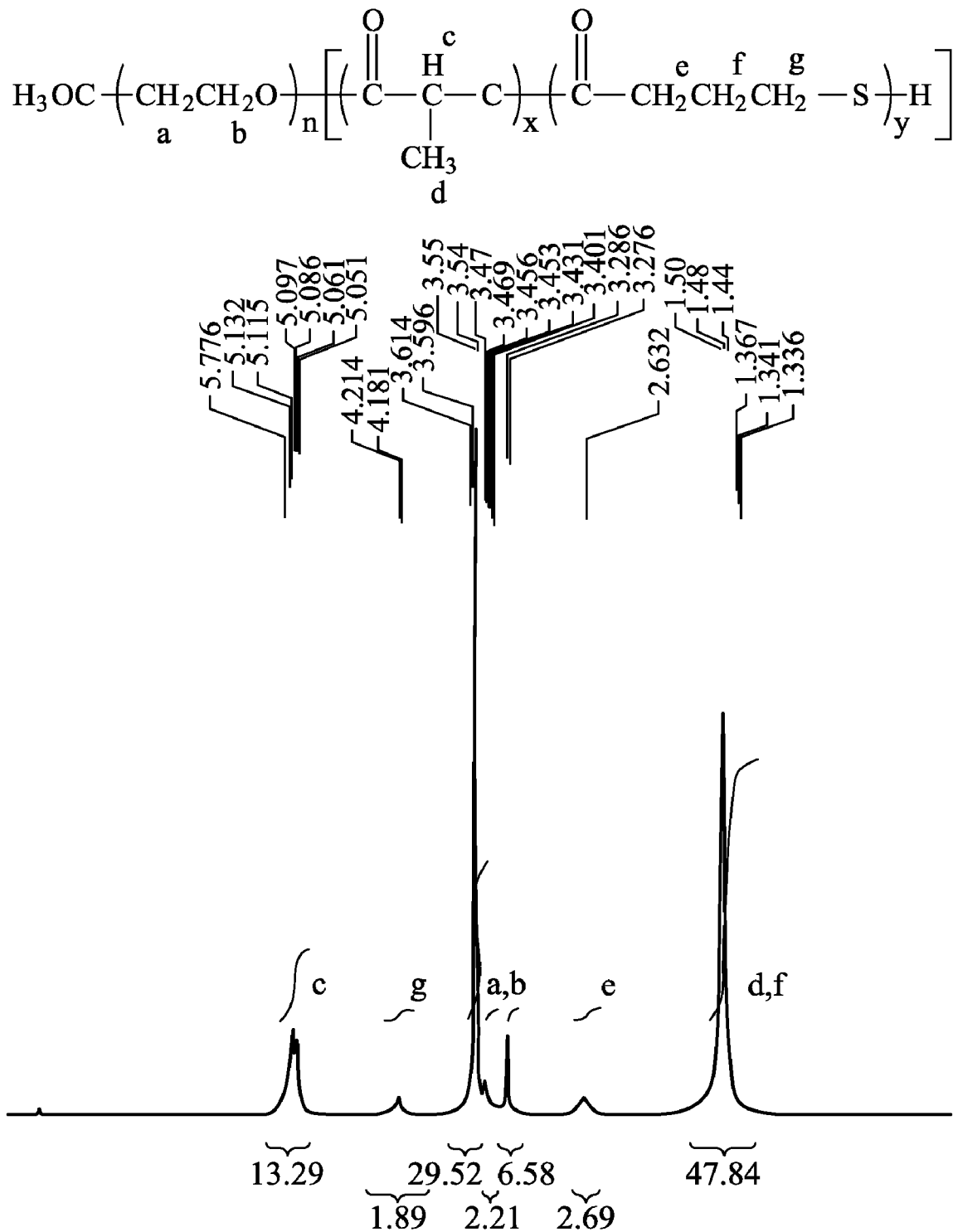
FIG. 14 is an NMR spectrum of mPEG-PSLA in one example of the invention.
Figure 15:
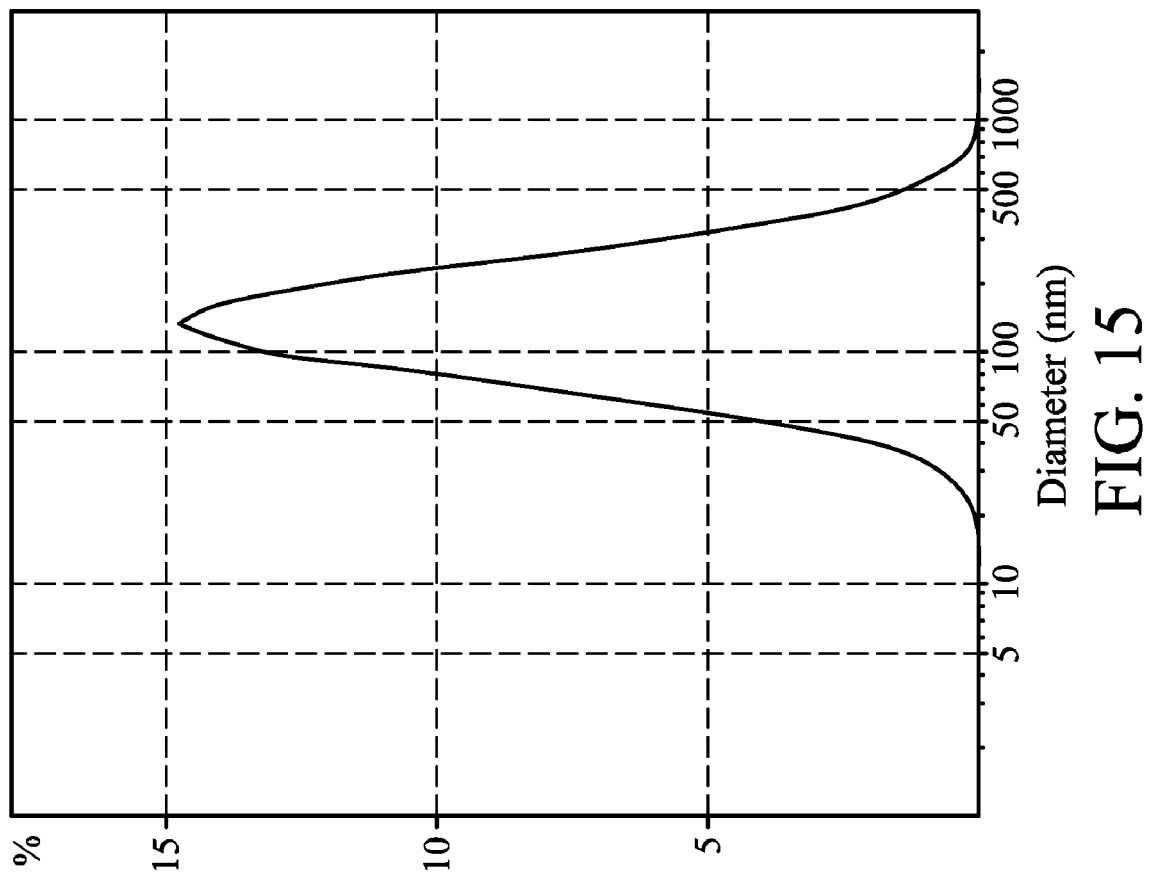
FIG. 15 is a micelle diameter distribution diagram of mPEG-PSLA in one example of the invention.
Figure 16:
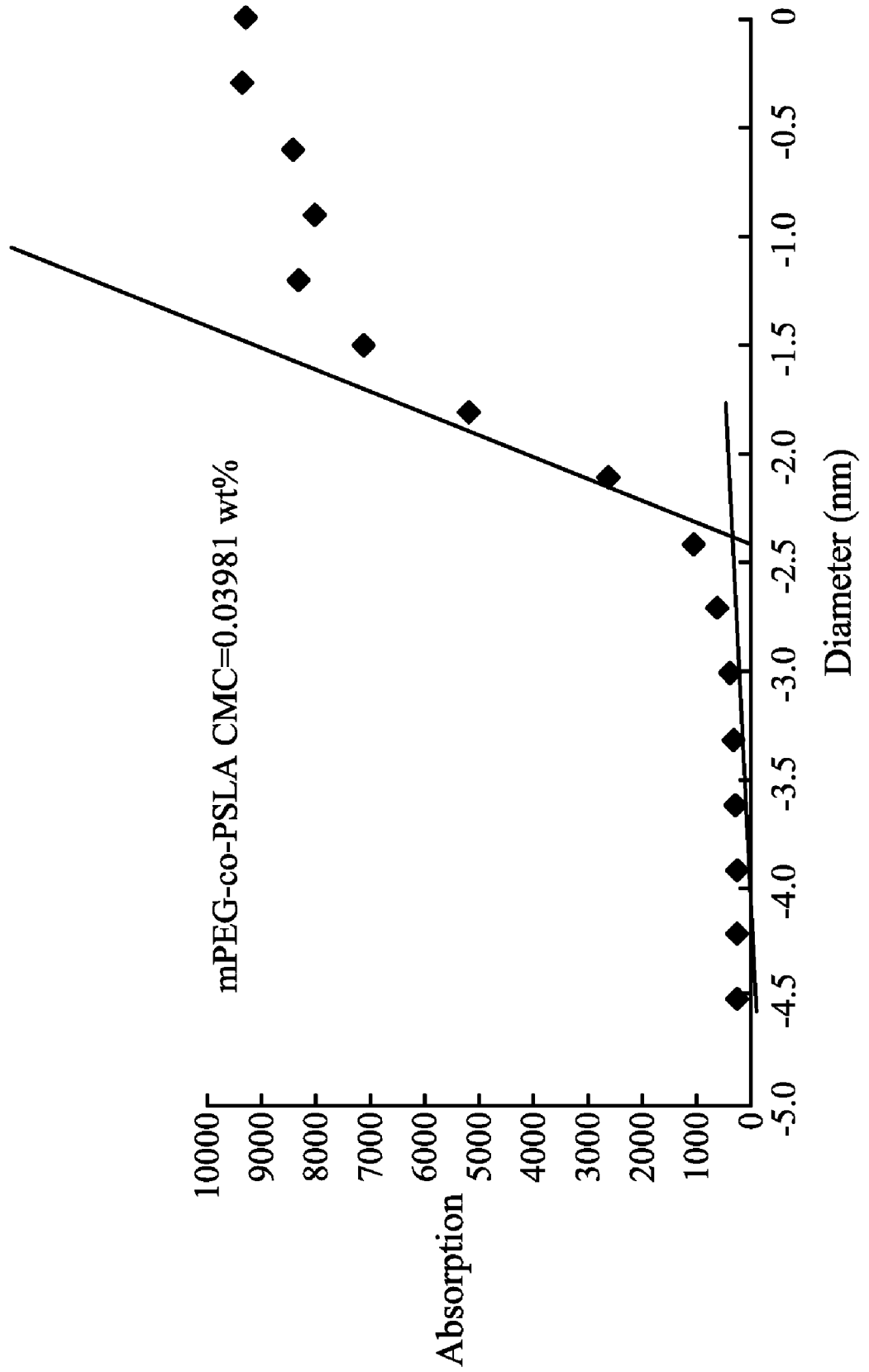
FIG. 16 is a critical micelle concentration diagram of mPEG-PSLA in one example of the invention.
Figure 17:
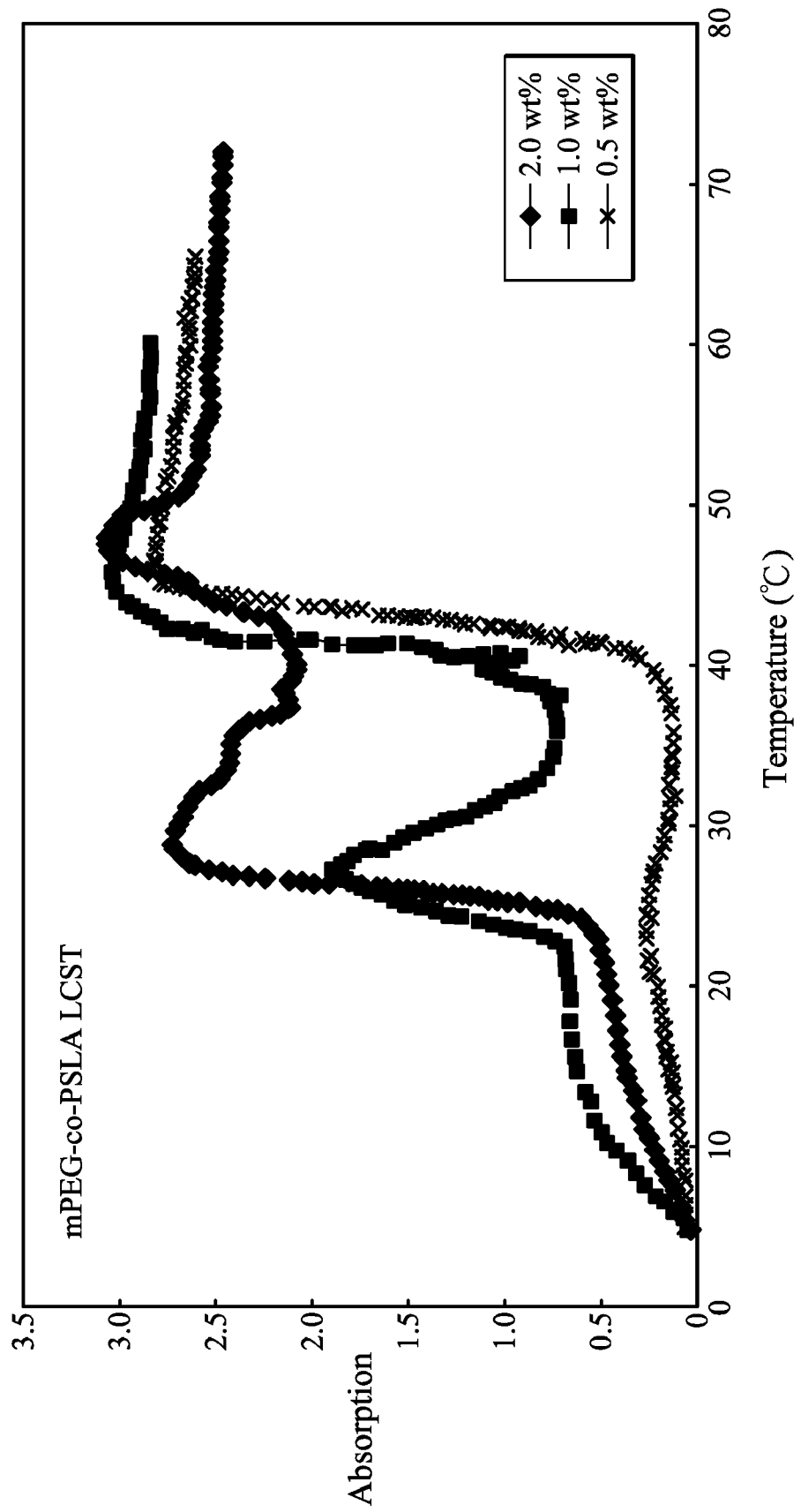
FIG. 17 is a UV transmittance versus temperature diagram of mPEG-PSLA in examples of the invention.
Figure 18:
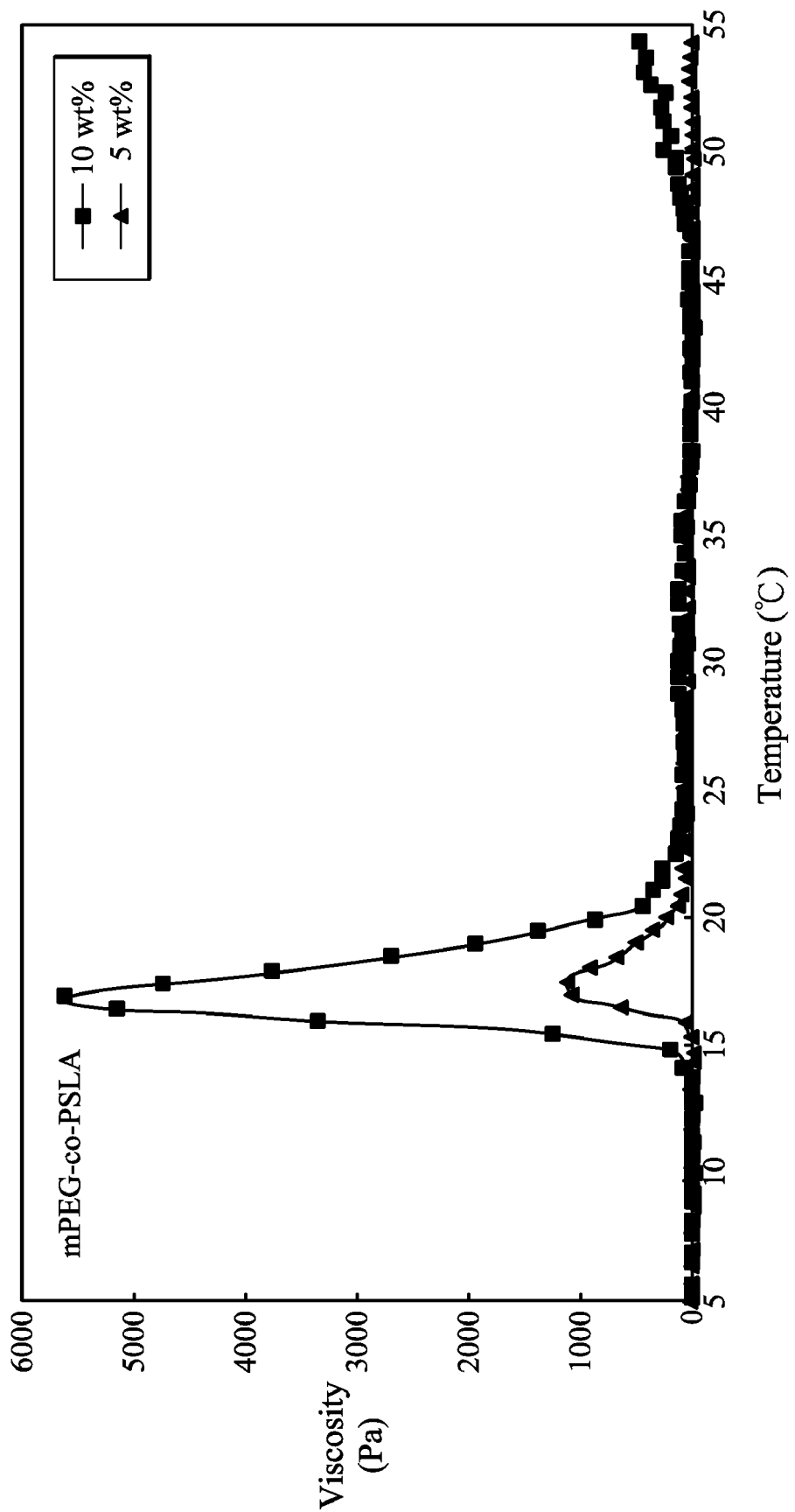
FIG. 18 is a viscosity versus temperature diagram of mPEG-PSLA in examples of the invention.
Figure 19:
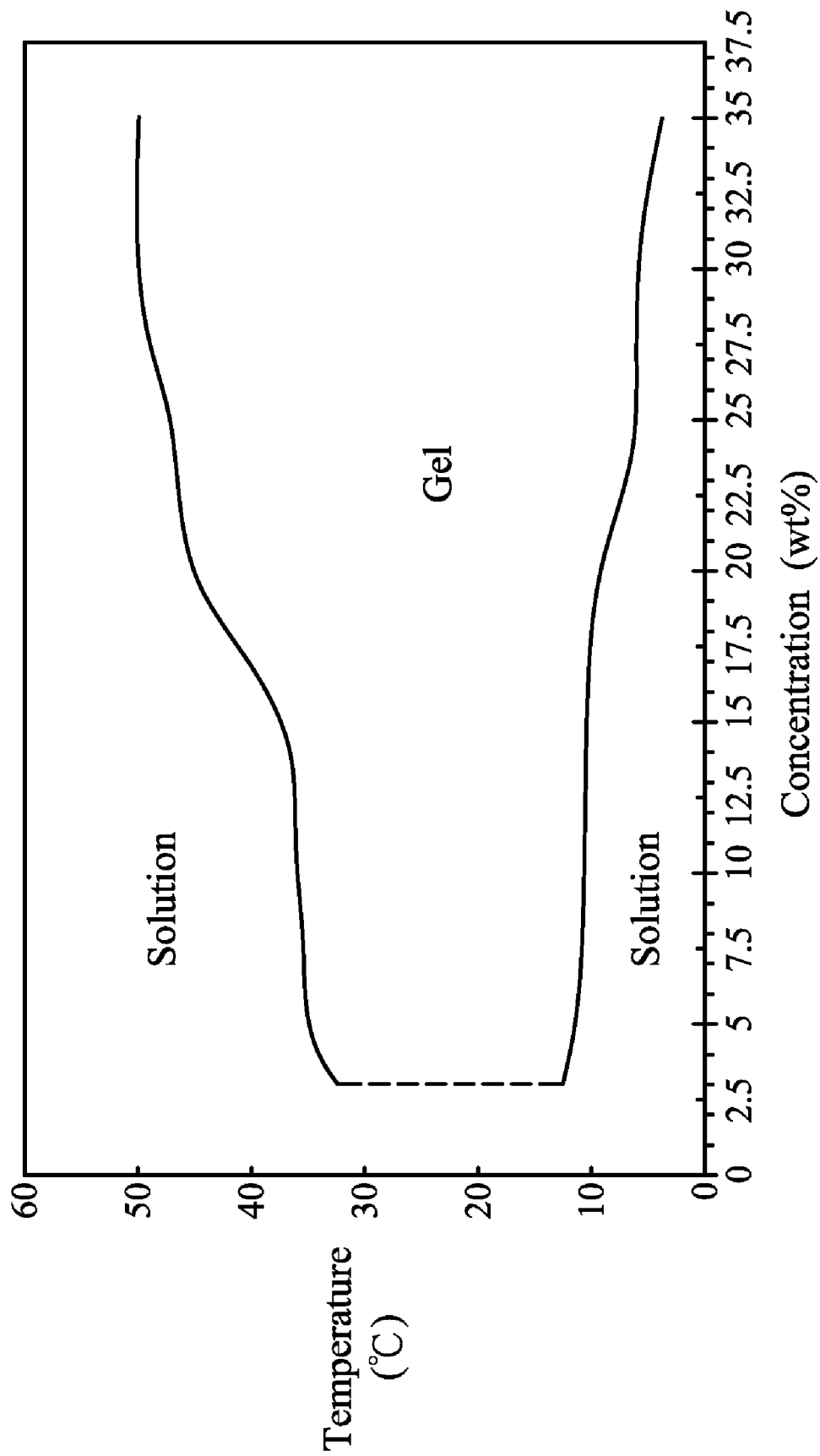
FIG. 19 is a Sol-Gel-Sol related to temperature and concentration of mPEG-PSLA in examples of the invention.

The copolymer mPEG-PSLA had an NMR spectrum as shown in FIG. 14, and a diameter analysis with instrument Zetasizer 1000H as shown in FIG. 15. The mPEG-PSLA dissolved in water is the thermosensitive material of the invention, the critical micelle concentration analysis is shown in FIG. 16, the UV transmittance related to temperature is shown in FIG. 17, and the viscosity related to temperature is shown in FIG. 18. Sol-Gel-Sol related to temperature and concentration is shown in FIG. 19. When the mPEG-PSLA liquid transformed to hydrogel, its UV transmittance was reduced. The thermosensitive material was a flowable transparent solution at a low temperature, a semi-transparent solution with higher viscosity at 25° C., and a non-flowable opaque hydrogel at 46° C. The gelling time of the mPEG-PSLA at 37° C. measured in a water sink was about 11.83 seconds.

Example 5

Copolymer of Methoxy Endcapped Polyethylene Glycol and Lactide/2-Iminothiolane Hydrochloride Random Copolymer, Hereinafter mPEG-PITLA 2.03 g of methoxy endcapped polyethylene glycol (mPEG, Molecular weight is 550 g/mol), 4.185 g of lactide, and 1 g of 2-Iminothiolane hydrochloride were subsequently charged in an anhydrous reactor, and the reactor temperature was slowly increased until the substances were totally dissolved. The temperature was continuously increased to 200° C., and 2.886 μL stannous catalyst (stannous 2-ethylhexanoate) was added in the reactor to process polymerization at 200° C. for 4 hours. The reaction is shown in Formula 10. The reaction result was precipitated in ethyl ether/hexane (volume ratio is 1:9) as a semitransparent brown gel. The semitransparent gel was washed three times to remove monomers and then dried in vacuum at 40° C. for 24 hours to obtain product mPEG-PITLA.

(Formula 10)

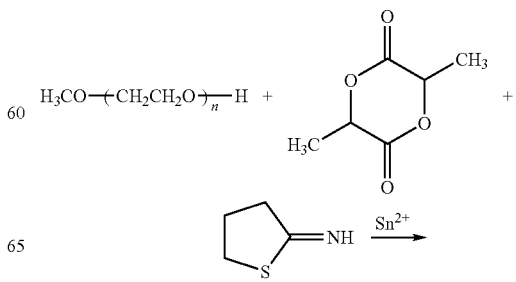

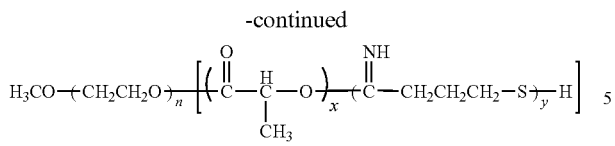

Figure 20:
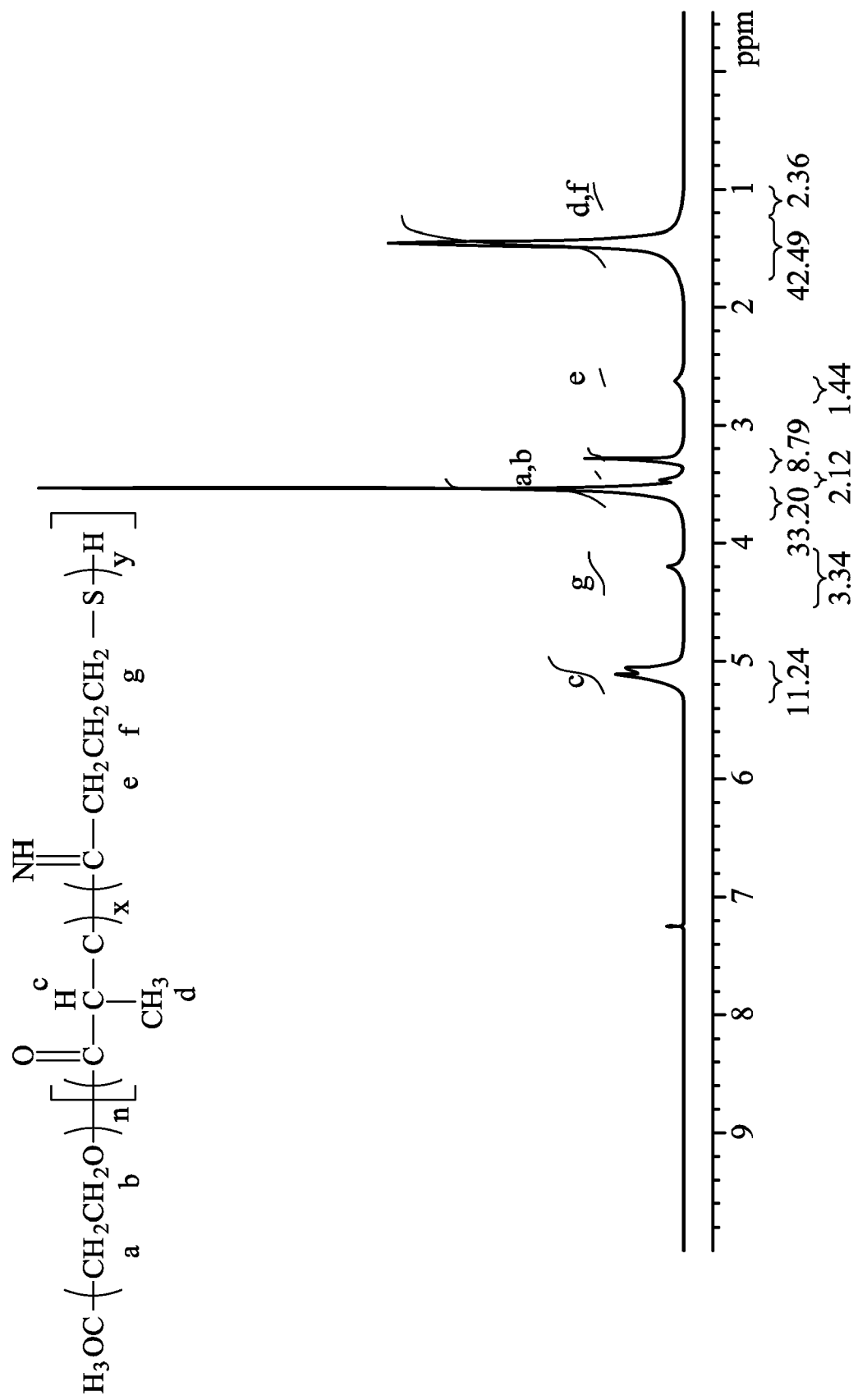
FIG. 20 is an NMR spectrum of mPEG-PITLA in one example of the invention.
Figure 21:
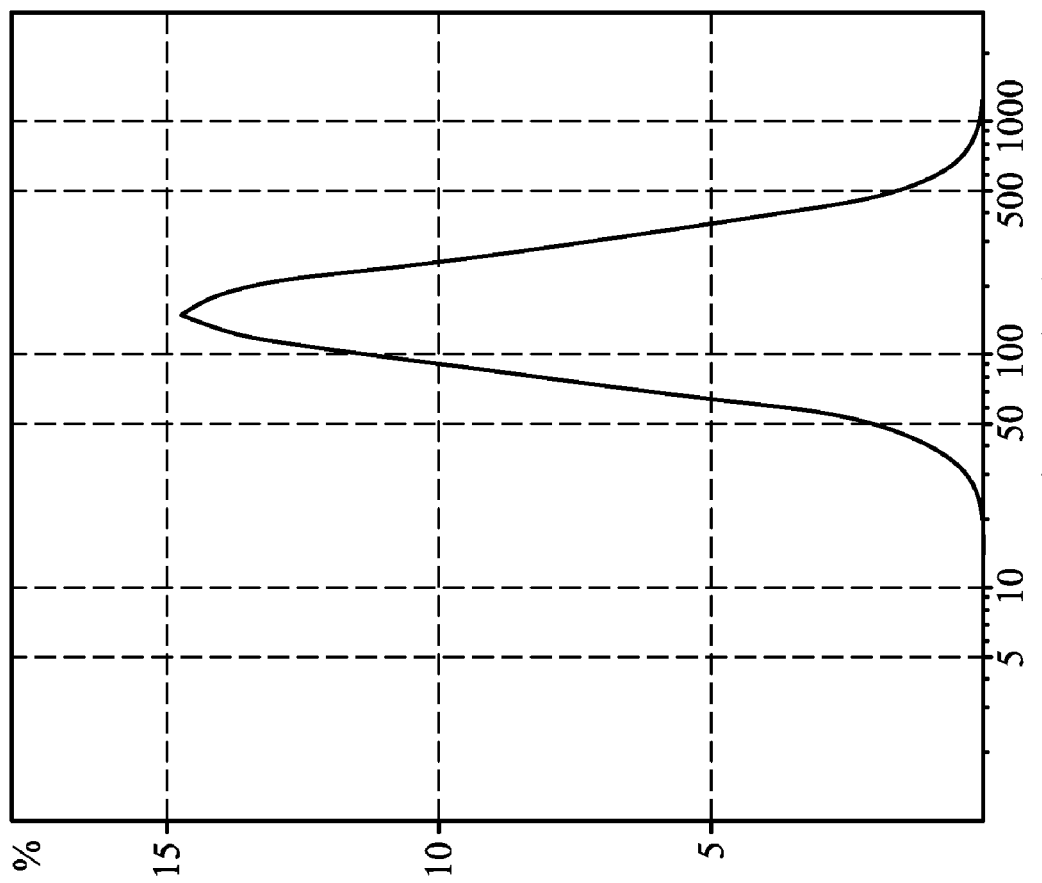
FIG. 21 is a micelle diameter distribution diagram of mPEG-PITLA in one example of the invention.
Figure 22:
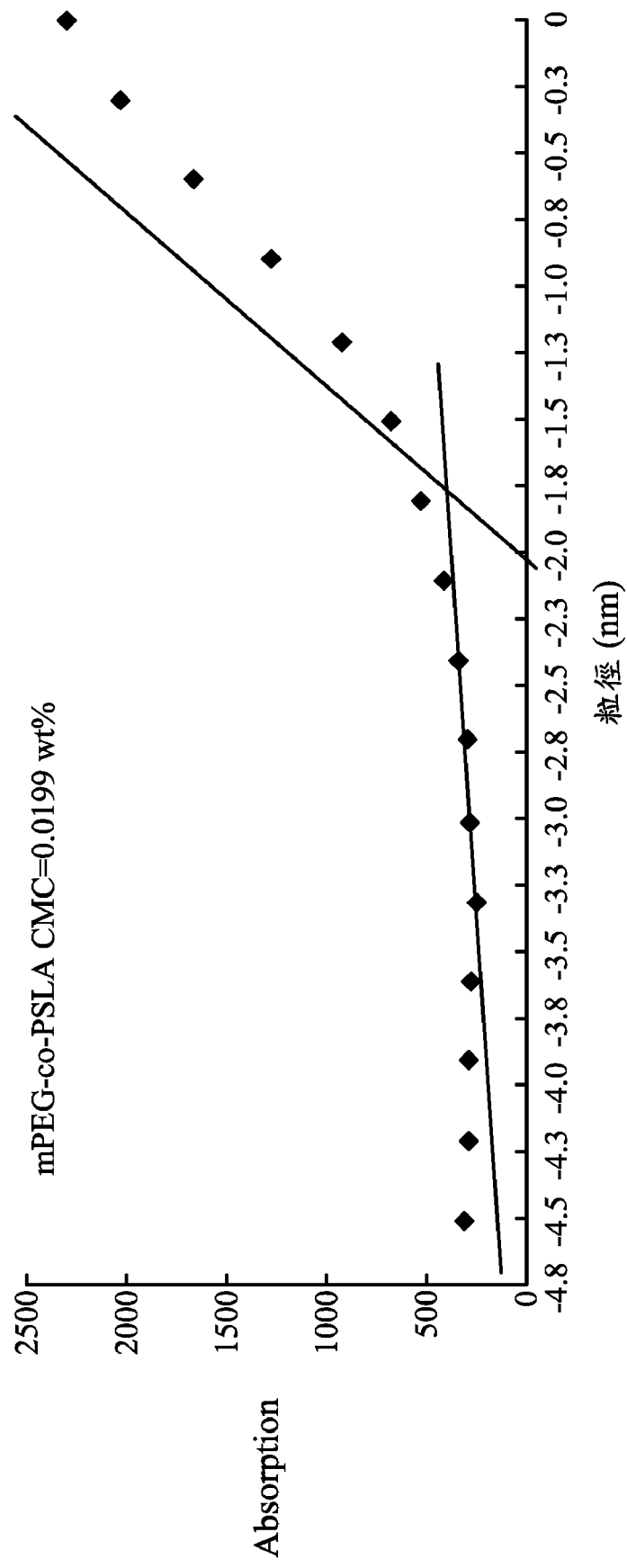
FIG. 22 is a critical micelle concentration diagram of mPEG-PITLA in one example of the invention.
Figure 23:
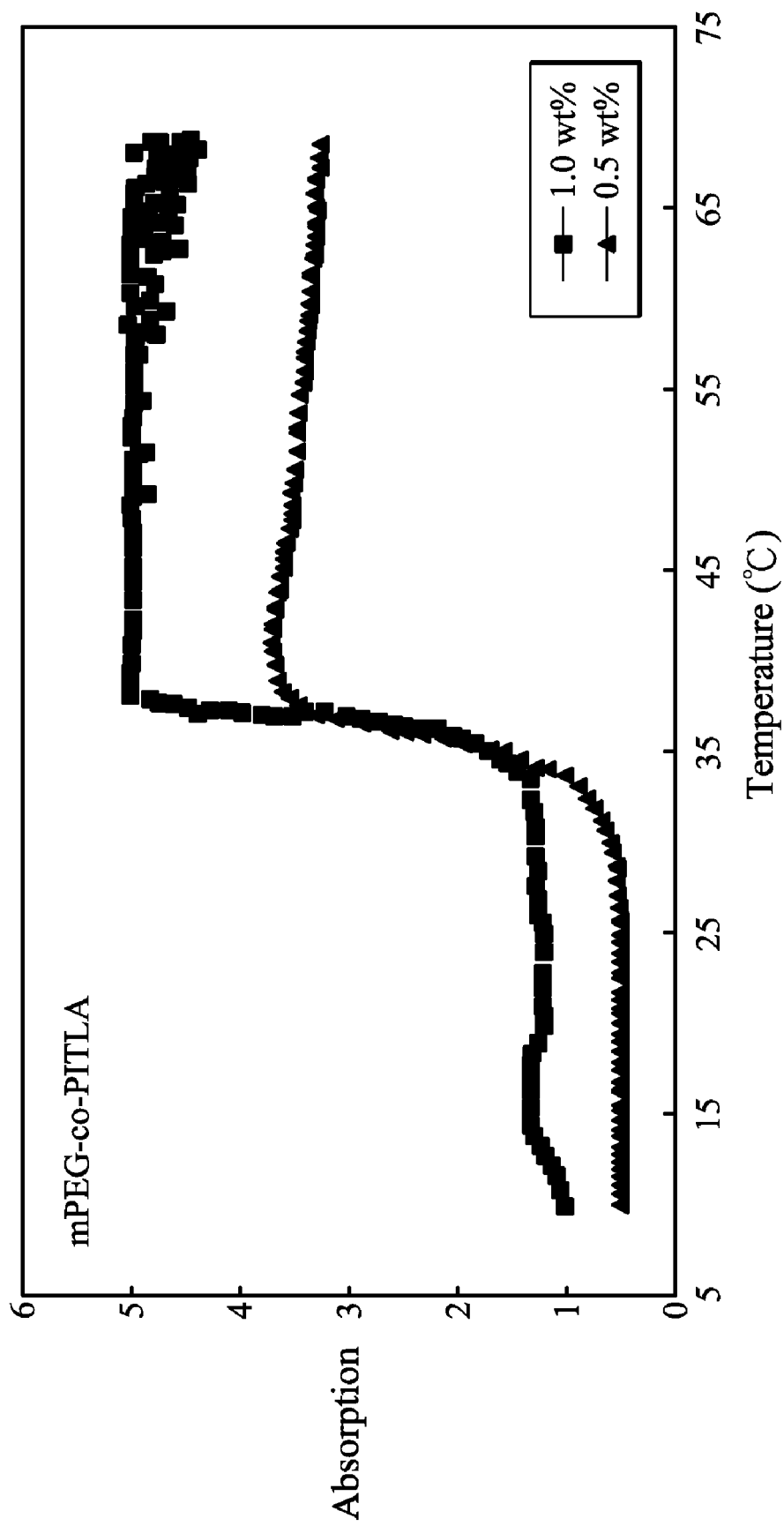
FIG. 23 is a UV transmittance versus temperature diagram of mPEG-PITLA in examples of the invention.
Figure 24:
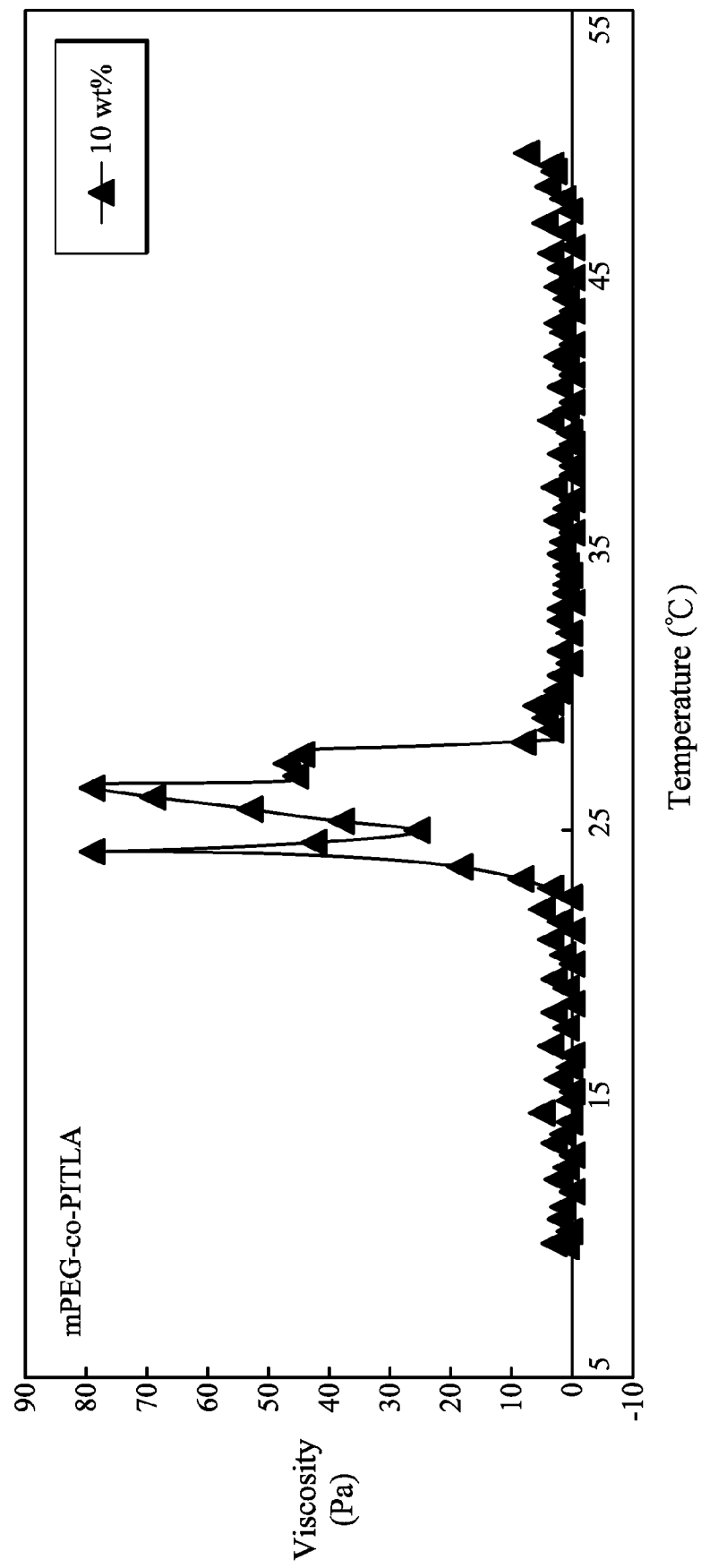
FIG. 24 is a viscosity versus temperature diagram of mPEG-PITLA in examples of the invention.

The copolymer mPEG-PITLA had an NMR spectrum as shown in FIG. 20, and a diameter analysis with instrument Zetasizer 1000H as shown in FIG. 21. The mPEG-PITLA dissolved in water is the thermosensitive material of the invention, the critical micelle concentration analysis is shown in FIG. 22, the UV transmittance related to temperature is shown in FIG. 23, and the viscosity related to temperature is shown in FIG. 24. When the mPEG-PITLA liquid transformed to hydrogel, its UV transmittance was reduced. The thermosensitive material was a flowable transparent solution at a low temperature, a semi-transparent solution with higher viscosity at 25° C., and a non-flowable opaque hydrogel at 40° C.

Example 6

Figure 25:
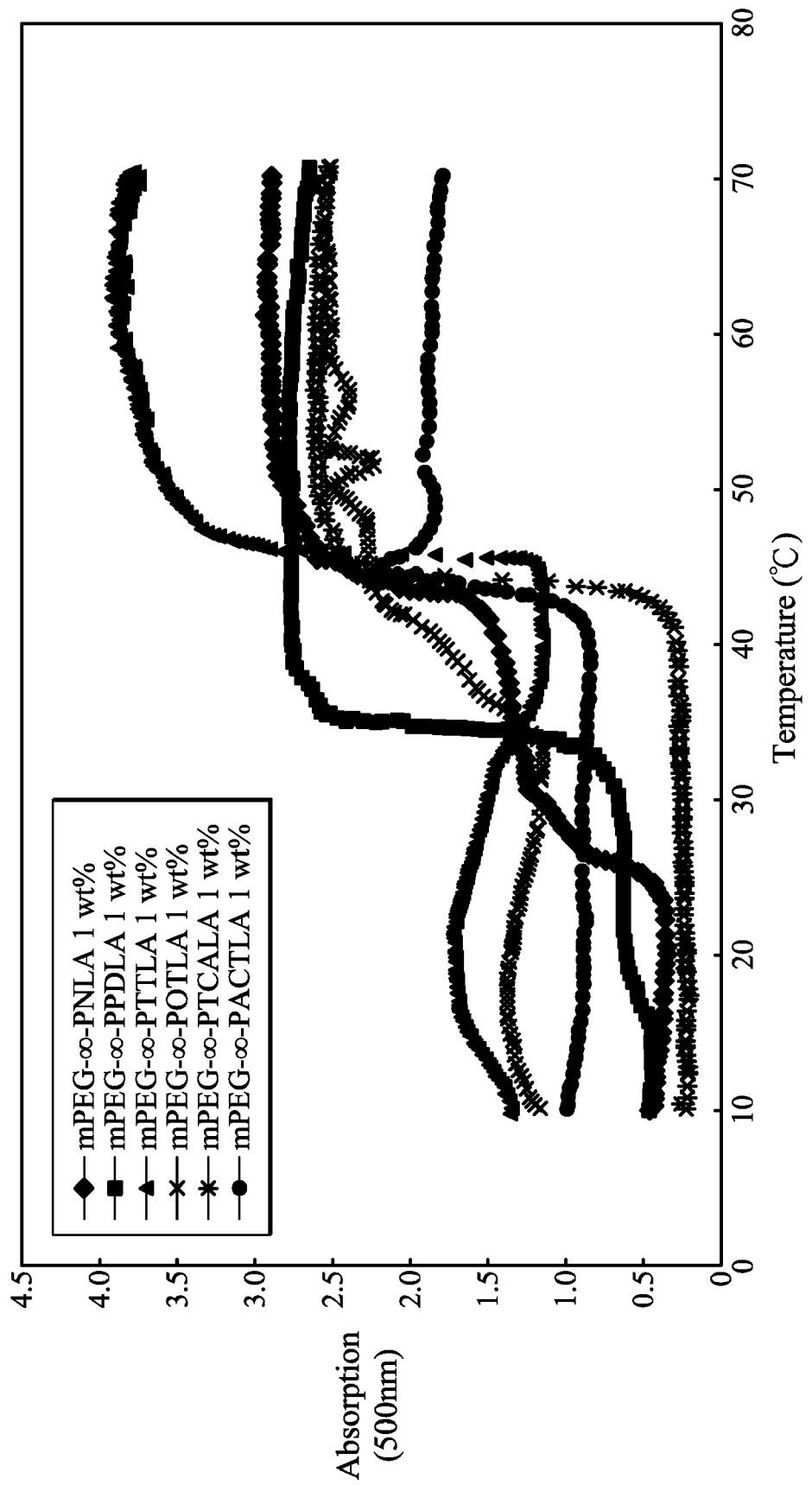
FIG. 25 is a UV transmittance versus temperature diagram of mPEG-PNLA, mPEG-PPDLA, mPEG-PTTLA, mPEG-POTLA, mPEG-PACTLA, mPEG-PTCALA in examples of the invention.

Copolymer of Methoxy Endcapped Polyethylene Glycol and Lactide/N-Methyl-2-Pyrrolidone Random Copolymer, Hereinafter mPEG-PNLA 7.99 g of methoxy endcapped polyethylene glycol (mPEG, Molecular weight is 550 g/mol), 17.43 g of lactide, and 3 g of N-Methyl-2-Pyrrolidone were subsequently charged in an anhydrous reactor, and the reactor temperature was slowly increased until the substances were totally dissolved. The temperature was continuously increased to 160° C., and 11.37 µL stannous catalyst (stannous 2-ethylhexanoate) was added in the reactor to process polymerization at 160° C. for 8 hours. The reaction is shown in Formula 11. The reaction result was precipitated in ethyl ether/hexane (volume ratio is 1:9) as a semitransparent brown gel. The semitransparent gel was washed three times to remove monomers and then dried in vacuum at 40° C. for 24 hours to obtain product mPEG-PNLA. The UV transmittance related to temperature is shown in FIG. 25.

(Formula 11)

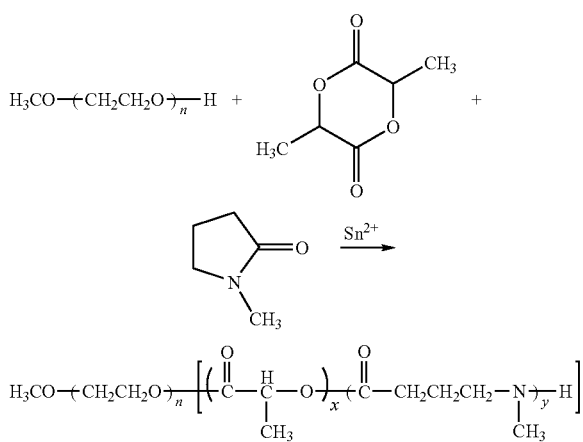

Example 7

Copolymer of Methoxy Endcapped Polyethylene Glycol and Lactide/γ-Butyrolactam Random Copolymer, Hereinafter mPEG-PPDLA 9.12 g of methoxy endcapped polyethylene glycol (mPEG, Molecular weight is 550 g/mol), 20.31 g of lactide, and 3 g of γ-butyrolactam were subsequently charged in an anhydrous reactor, and the reactor temperature was slowly increased until the substances were totally dissolved. The temperature was continuously increased to 160° C., and 12.97 µL stannous catalyst (stannous 2-ethylhexanoate) was added in the reactor to process polymerization at 160° C. for 8 hours. The reaction is shown in Formula 12. The reaction result was precipitated in ethyl ether/hexane (volume ratio is 1:9) as a semitransparent brown gel. The semitransparent yellow gel was washed three times to remove monomers and then dried in vacuum at 40° C. for 24 hours to obtain product mPEG-PPDLA. The UV transmittance related to temperature is shown in FIG. 25

(Formula 12)

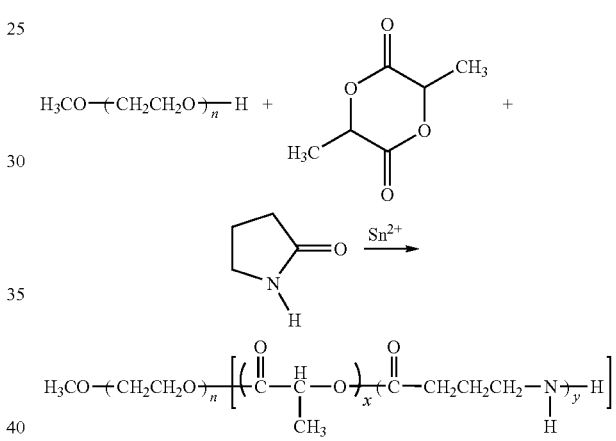

Example 8

Copolymer of Methoxy Endcapped Polyethylene Glycol and Lactide/(−)-2-Oxo-4-Thiazolidinecarboxylic Acid Random Copolymer, Hereinafter mPEG-POTLA 4.81 g of methoxy endcapped polyethylene glycol (mPEG, Molecular weight is 550 g/mol), 9.79 g of lactide, and 2.5 g of (−)-2-Oxo-4-thiazolidinecarboxylic acid were subsequently charged in an anhydrous reactor, and the reactor temperature was slowly increased until the substances were totally dissolved. The temperature was continuously increased to 180° C., and 6.838 µL stannous catalyst (stannous 2-ethylhexanoate) was added in the reactor to process polymerization at 180° C. for 8 hours. The reaction is shown in Formula 13. The reaction result was precipitated in ethyl ether/hexane (volume ratio is 1:9) as a semitransparent brown gel. The semitransparent yellow gel was washed three times to remove monomers and then dried in vacuum at 40° C. for 24 hours to obtain product mPEG-POTLA. The UV transmittance related to temperature is shown in FIG. 25.

(Formula 13)

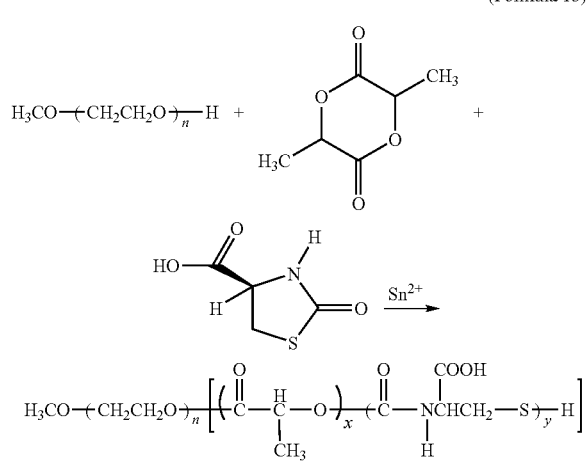

Example 9

Copolymer of Methoxy Endcapped Polyethylene Glycol and Lactide/(4R)-(−)-2-Thioxo-4-Thiazolidinecarboxylic Acid Random Copolymer, Hereinafter mPEG-PTTLA 2.31 g of methoxy endcapped polyethylene glycol (mPEG, Molecular weight is 550 g/mol), 4.59 g of lactide, and 1.3 g of (4R)-(−)-2-Thioxo-4-thiazolidinecarboxylic acid were subsequently charged in an anhydrous reactor, and the reactor temperature was slowly increased until the substances were totally dissolved. The temperature was continuously increased to 180° C., and 3.277 μL stannous catalyst (stannous 2-ethylhexanoate) was added in the reactor to process polymerization at 180° C. for 8 hours. The reaction is shown in Formula 14. The reaction result was precipitated in ethyl ether/hexane (volume ratio is 1:9) as a semitransparent brown gel. The semitransparent brown gel was washed three times to remove monomers and then dried in vacuum at 40° C. for 24 hours to obtain product mPEG-PTTLA. The UV transmittance related to temperature is shown in FIG. 25.

(Formula 14)

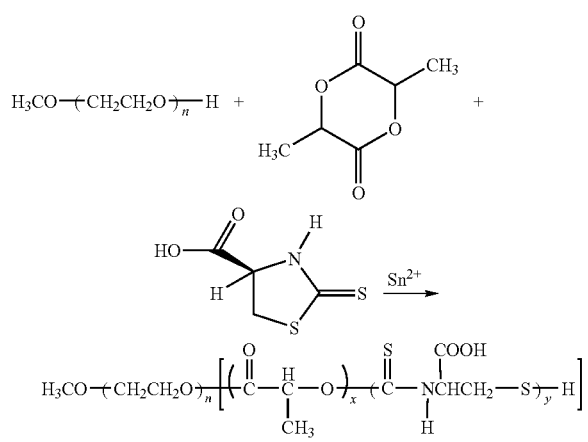

Example 10

Copolymer of Methoxy Endcapped Polyethylene Glycol and Lactide/DL-N-Acetylhomocysteine Thiolactone Random Copolymer, Hereinafter mPEG-PACTLA 9.04 g of methoxy endcapped polyethylene glycol (mPEG, Molecular weight is 550 g/mol), 18.09 g of lactide, and 5 g of DL-N-Acetylhomocysteine thiolactone were subsequently charged in an anhydrous reactor, and the reactor temperature was slowly increased until the substances were totally dissolved. The temperature was continuously increased to 160° C., and 12.86 μL stannous catalyst (stannous 2-ethylhexanoate) was added in the reactor to process polymerization at 160° C. for 8 hours. The reaction is shown in Formula 15. The reaction result was precipitated in ethyl ether/hexane (volume ratio is 1:9) as a semitransparent yellow gel. The semitransparent brown gel was washed three times to remove monomers and then dried in vacuum at 40° C. for 24 hours to obtain product mPEG-PACTLA. The UV transmittance related to temperature is shown in FIG. 25.

(Formula 15)

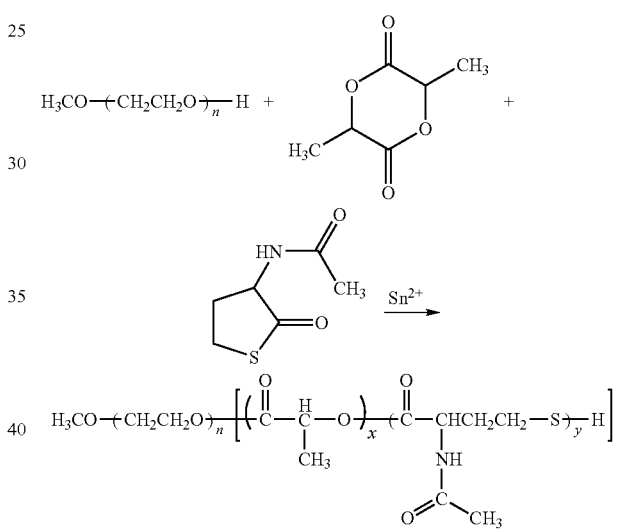

Example 11

Copolymer of Methoxy Endcapped Polyethylene Glycol and Lactide/5-Thiazolecarboxaldehyde Random Copolymer, Hereinafter mPEG-PTCALA 2.384 g of methoxy endcapped polyethylene glycol (mPEG, Molecular weight is 550 g/mol), 5.09 g of lactide, and 1 g of 5-Thiazolecarboxaldehyde were subsequently charged in an anhydrous reactor, and the reactor temperature was slowly increased until the substances were totally dissolved. The temperature was continuously increased to 160° C., and 3.39 μL stannous catalyst (stannous 2-ethylhexanoate) was added in the reactor to process polymerization at 160° C. for 8 hours. The reaction is shown in Formula 16. The reaction result was precipitated in ethyl ether/hexane (volume ratio is 1:9) as a semitransparent yellow gel. The semitransparent yellow gel was washed three times to remove monomers and then dried in vacuum at 40° C. for 24 hours to obtain product mPEG-PTCALA. The UV transmittance related to temperature is shown in FIG. 25.

(Formula 16)

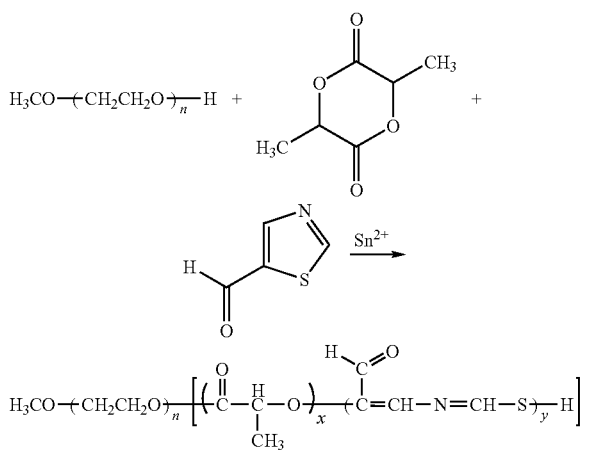

Comparative Example 1

Copolymer of Methoxy Endcapped Polyethylene Glycol and Lactide, Hereinafter mPEG-PLA 17.36 g of methoxy endcapped polyethylene glycol (mPEG, Molecular weight is 550 g/mol) and 50 g of lactide were subsequently charged in an anhydrous reactor, and the reactor temperature was slowly increased until the substances were totally dissolved. The temperature was continuously increased to 160° C., and 34.0 μL stannous catalyst (stannous 2-ethylhexanoate) was added in the reactor to process polymerization at 160° C. for 8 hours. The reaction is shown in Formula 17. The reaction result was precipitated in ethyl ether/hexane (volume ratio is 1:9) as a semitransparent gel. The semitransparent gel was washed three times to remove monomers and then dried in vacuum at 40° C. for 24 hours to obtain product mPEG-PLA.

(Formula 17)

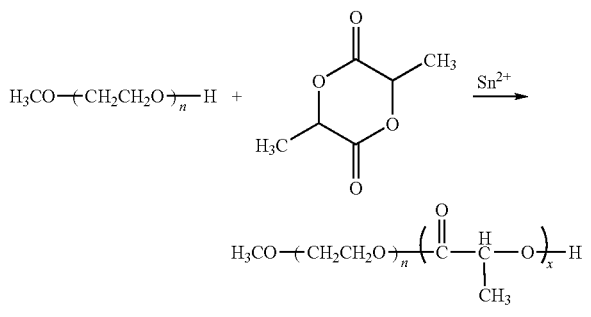

Figure 26:
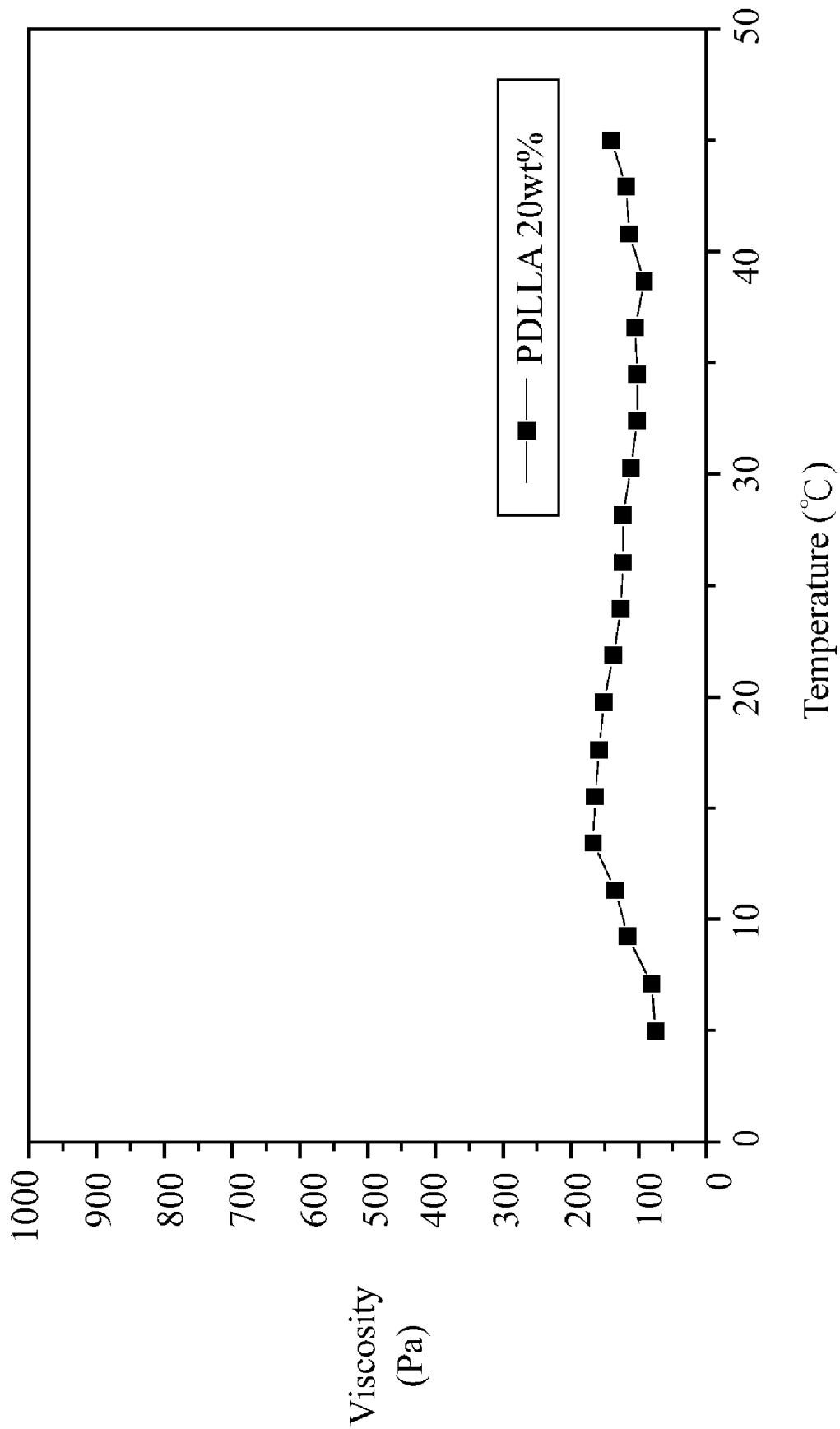
FIG. 26 is a viscosity versus temperature diagram of mPEG-PLA in one comparative example of the invention.

The mPEG-PLA solution viscosity was measured as shown in FIG. 26. Even if the solution was heated to 45° C., the solution viscosity does not remarkably change. Accordingly, the lactone is necessary to copolymerize with the lactide for completing the hydrophobic segment. If the hydrophobic segment is only polymerized by lactide, the diblock copolymer composed of methoxy endcapped polyethylene glycol and polylactide will not have thermosensitivity.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A biodegradable copolymer, having a general formula $$A\text{---}[B]$$

in which:

A- is a hydrophilic segment selected from those having a formula:

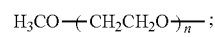

—B is a hydrophobic segment selected from segments such that the biodegradable copolymer is selected from those having a formula:

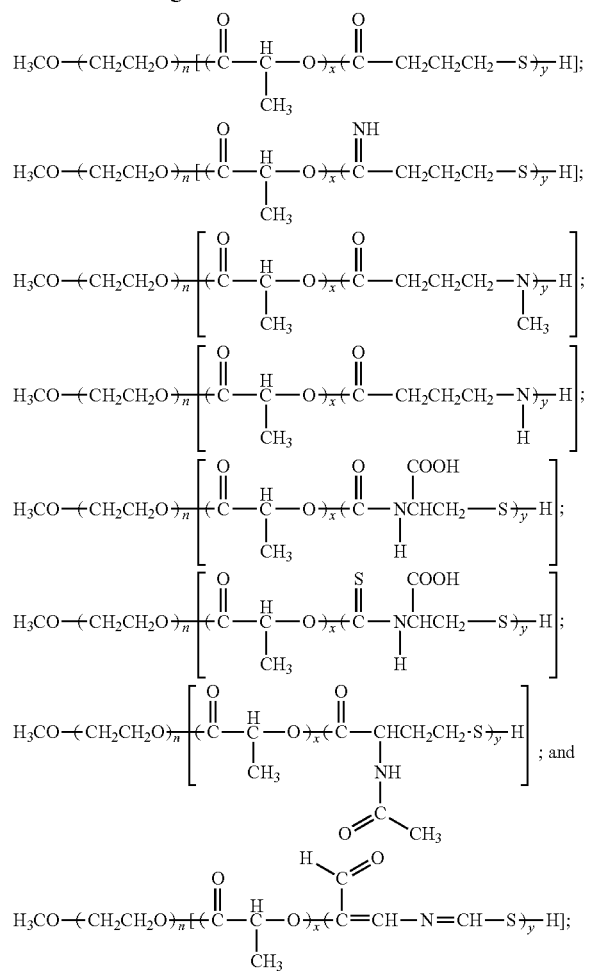

$n$ is an integer of 5-20;
$x$ is an integer of 5-20; and
$y$ is an integer of 5-20.

2. The biodegradable copolymer as claimed in claim 1, wherein the hydrophilic segment A- of the biodegradable copolymer has a molecular weight of 300 to 1000.

3. The biodegradable copolymer as claimed in claim 1, wherein the hydrophobic segment —B of the biodegradable copolymer has a molecular weight of 800 to 2000.

4. The biodegradable copolymer as claimed in claim 1, wherein x is greater than or equal to y.

5. The biodegradable copolymer as claimed in claim 1, wherein x and y has a molar ratio of 50:50 to 90:10.

6. A thermosensitive material, comprising:
water; and
the biodegradable copolymer as claimed in claim 1 dissolved in the water to form a solution,
wherein the hydrophobic segment —B aggregates to form micelles.

7. The thermosensitive material as claimed in claim 6, wherein the biodegradable material and the water have a weight ratio of 2:98 to 40:60.

8. The thermosensitive material as claimed in claim 6, wherein the biodegradable material and the water have a weight ratio of 15:85 to 30:70.

9. The thermosensitive material as claimed in claim 6, wherein the micelles have a diameter of 5 nm to 500 nm.

10. The thermosensitive material as claimed in claim 6, further having a phase transfer temperature of 25 to 50° C.

11. The thermosensitive material as claimed in claim 6, further having a phase transfer temperature of 30 to 40° C.

12. The thermosensitive material as claimed in claim 6 is applied through injection, pastille, powder, gel, solution, or oral liquid.

13. The biodegradable copolymer as claimed in claim 1, wherein the hydrophobic segment —B has a formula:

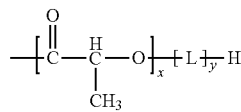

in which:
L is synthesized from a lactone or a $C_3$-$C_6$ molecule selected from, γ-thiobutyrolactone, 2 iminothiolane hydrochloride, (4R)-(−)-2-thioxo-4-thiazolidinecarboxylic acid, (−)-2-oxo-4-thiazolidinecarboxylic acid, DL-N-acetylhomocysteine thiolactone, 5-thiazolecarboxaldehyde, γ-butyrolactam, and 1-methyl-2-pyrrolidinone;
x is an integer of 5-20; and
y is an integer of 5-20.

14. The biodegradable copolymer as claimed in claim 1, wherein the biodegradable copolymer is selected from those having a formula:

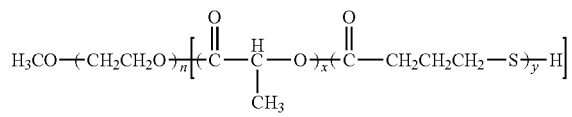

in which:
n is an integer of 5-20;
x is an integer of 5-20; and
y is an integer of 5-20.

15. The biodegradable copolymer as claimed in claim 1, wherein the biodegradable copolymer is selected from those having a formula:

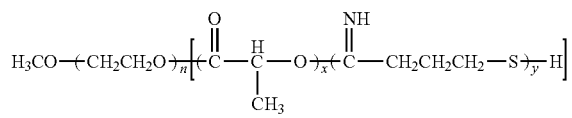

in which:
n is an integer of 5-20;
x is an integer of 5-20; and
y is an integer of 5-20.

16. The biodegradable copolymer as claimed in claim 1, wherein the biodegradable copolymer is selected from those having a formula:

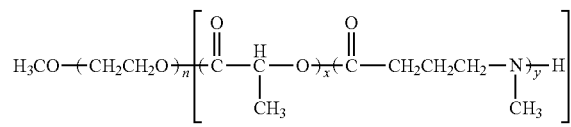

in which:
n is an integer of 5-20;
x is an integer of 5-20; and
y is an integer of 5-20.

17. The biodegradable copolymer as claimed in claim 1, wherein the biodegradable copolymer is selected from those having a formula:

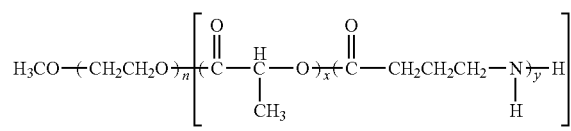

in which:
n is an integer of 5-20;
x is an integer of 5-20; and
y is an integer of 5-20.

18. The biodegradable copolymer as claimed in claim 1, wherein the biodegradable copolymer is selected from those having a formula:

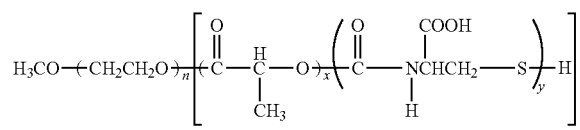

in which:
n is an integer of 5-20;
x is an integer of 5-20; and
y is an integer of 5-20.

19. The biodegradable copolymer as claimed in claim 1, wherein the biodegradable copolymer is selected from those having a formula:

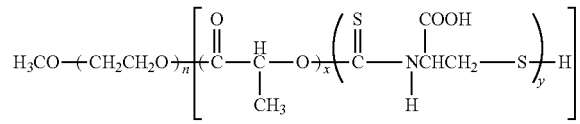

in which:
n is an integer of 5-20;
x is an integer of 5-20; and
y is an integer of 5-20.

20. The biodegradable copolymer as claimed in claim 1, wherein the biodegradable copolymer is selected from those having a formula:

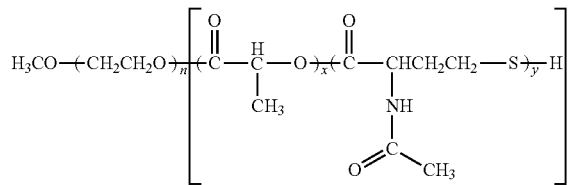

in which:
   n is an integer of 5-20;
   x is an integer of 5-20; and
   y is an integer of 5-20.

21. The biodegradable copolymer as claimed in claim 1, wherein the biodegradable copolymer is selected from those having a formula:

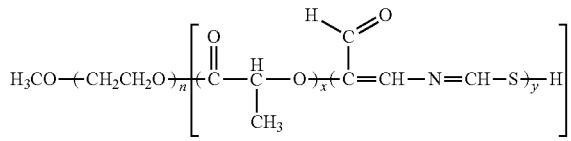

in which:
   n is an integer of 5-20;
   x is an integer of 5-20; and
   y is an integer of 5-20.

* * * * *

UNITED STATES PATENT AND TRADEMARK OFFICE
CERTIFICATE OF CORRECTION

PATENT NO. : 7,884,142 B2  Page 1 of 1
APPLICATION NO. : 12/395495
DATED : February 8, 2011
INVENTOR(S) : Ya-Jen Yu et al.

It is certified that error appears in the above-identified patent and that said Letters Patent is hereby corrected as shown below:

On the title page insert the Foreign Application Priority Data

ITEM --[30]   March 28, 2008 (TW) 097111275

October 28, 2008 (TW) 097141336--

Signed and Sealed this
Tenth Day of May, 2011

David J. Kappos
*Director of the United States Patent and Trademark Office*